(12) United States Patent
Holtzman et al.

(10) Patent No.: US 7,195,761 B2
(45) Date of Patent: Mar. 27, 2007

(54) HUMANIZED ANTIBODIES THAT SEQUESTER ABETA PEPTIDE

(75) Inventors: David M. Holtzman, St. Louis, MO (US); Ronald DeMattos, Noblesville, IN (US); Kelly R. Bales, Indianapolis, IN (US); Steven M. Paul, Carmel, IN (US); Naoya Tsurushita, Palo Alto, CA (US); Maximiliano Vasquez, Palo Alto, CA (US)

(73) Assignees: Eli Lilly and Company, Indianapolis, IN (US); Washington University, St. Louis, MO (US)

( * ) Notice: Subject to any disclaimer, the term of this patent is extended or adjusted under 35 U.S.C. 154(b) by 0 days.

(21) Appl. No.: 10/226,435

(22) Filed: Aug. 22, 2002

(65) Prior Publication Data

US 2004/0043418 A1    Mar. 4, 2004

Related U.S. Application Data

(63) Continuation of application No. PCT/US01/06191, filed on Feb. 26, 2001.

(60) Provisional application No. 60/184,601, filed on Feb. 24, 2000, provisional application No. 60/256,465, filed on Dec. 8, 2000, provisional application No. 60/254,498, filed on Dec. 8, 2000.

(51) Int. Cl.
*C07K 16/18* (2006.01)
*A61K 39/395* (2006.01)

(52) U.S. Cl. .............. 424/133.1; 424/139.1; 530/387.3; 530/388.85

(58) Field of Classification Search ........... 530/387.1, 530/387.3, 387.9, 388.1, 388.25, 389.1, 390.5; 536/23.1, 23.5; 435/69.1, 320.1; 424/141.1, 424/145.1, 142.1, 130.1, 139.1, 140.1
See application file for complete search history.

(56) References Cited

U.S. PATENT DOCUMENTS

| | | | |
|---|---|---|---|
| 5,004,697 A | | 4/1991 | Pardridge |
| 5,278,049 A | * | 1/1994 | Baker et al. ............. 435/69.2 |
| 5,593,846 A | | 1/1997 | Schenk et al. |
| 5,688,651 A | | 11/1997 | Solomon |
| 5,693,762 A | * | 12/1997 | Queen et al. ............ 530/387.3 |
| 5,753,624 A | | 5/1998 | McMichael et al. |
| 5,766,846 A | | 6/1998 | Schlossmacher et al. |
| 5,837,672 A | | 11/1998 | Schenk et al. |
| 5,837,822 A | * | 11/1998 | Gallatin et al. .......... 530/387.3 |
| 5,851,996 A | | 12/1998 | Kline |
| 5,935,927 A | | 8/1999 | Vitek et al. |
| 6,037,454 A | * | 3/2000 | Jardieu et al. ........... 530/387.3 |
| 6,114,113 A | | 9/2000 | McLaughlin-Taylor et al. |
| 6,218,506 B1 | | 4/2001 | Krafft et al. |
| 2002/0009445 A1 | | 1/2002 | Yansheng et al. |
| 2002/0058267 A1 | | 5/2002 | Ozenberger et al. |
| 2002/0086847 A1 | | 7/2002 | Chain |
| 2002/0102261 A1 | | 8/2002 | Raso |

FOREIGN PATENT DOCUMENTS

| | | |
|---|---|---|
| EP | 0613007 | 2/1994 |
| WO | WO89/01343 | 2/1989 |
| WO | WO96/18900 | 6/1996 |
| WO | WO96/25435 | 8/1996 |
| WO | WO98/33815 | 8/1998 |
| WO | WO98/44955 | 10/1998 |
| WO | WO99/27944 | 6/1999 |
| WO | WO99/06066 | 11/1999 |
| WO | WO99/60024 | 11/1999 |
| WO | WO00/72876 A2 | 12/2000 |
| WO | WO00/72880 A2 | 12/2000 |
| WO | WO00/77178 A1 | 12/2000 |
| WO | WO01/10900 | 2/2001 |
| WO | WO01/18169 | 3/2001 |
| WO | WO02/021141 | 3/2002 |
| WO | WO02/046237 | 6/2002 |
| WO | WO02/060481 A1 | 8/2002 |

OTHER PUBLICATIONS

Shefner et al., J. Exp. Med., 173:287-296, 1991, Ig kappa(light) chain v region.*
Adair et al., WO 91/09967.*
Raaphorst et al., Eur. J. Immunol., 22, 247-251, 1992, Ig heavy chain.*
Strbak, V. et al. "Passive Immunization and Hypothalamic peptide Secretion", Neuroendocrinology 1993; 58:210-217.
Ragusi, C. et al. "Redistribution of Imipramine from Regions of the Brain Under the Influence of Circulating Specific Antibodies" J. Neurochem., vol. 70, No. 5, pp. 2099-105 (1998) The form should be signed and dated by.
Suo, Z. et al., "Soluble Alzhelmers β-amyloid constricts the cerebral vasculature in vivo" Neuroscience Letters 257, pp. 77-80 (1998).
Lue, L. et al., "Soluble β-amyloidPeptide Concentration as a Predictor of Synaptic Change in Alzheimer's Disease", Am. J. Pathol. 1999, 155: pp. 853-62.
Teller, J. et al. "Presence of soluble amyloid β-peptide precedes amyloid plague formation in Down's syndrome" Nature Medicine, vol. 2, No. 1, pp. 93-95 (1996).
Esler, W. et al. "Point substitution in the central hydrophobic cluster of a human β-amyloid congener disrupts peptide folding and abolishes plaque competence" Biochemistry, vol. 35, pp. 13914-21 (1996).

(Continued)

*Primary Examiner*—Elizabeth Kemmerer
*Assistant Examiner*—Kimberly A. Ballard
(74) *Attorney, Agent, or Firm*—Mark J. Stewart

(57) ABSTRACT

A method to treat conditions characterized by formation of amyloid plaques both prophylactically and therapeutically is described. The method employs humanized antibodies which sequester soluble Aβ peptide from human biological fluids or which preferably specifically bind an epitope contained within position 13–28 of the amyloid beta peptide Aβ.

12 Claims, 6 Drawing Sheets

OTHER PUBLICATIONS

Maggio, J. & Mantyh, P. "Brain Amyloid—A Physicochemical Perspective" *Brain Pathology*, vol. 6, 147-162 (1996).

Gorevic, P. et al. "Ten to fourteen residue peptides of Alzheimer's disease protein are sufficient for amyloid fibril formation and its characteristic X ray diffraction pattern" Biochem. and Biophy. Res. Commun., vol. 147, No. 2 (1987).

Balbach, J. et al. "Amyloid fibril formation by $A\beta_{16-22}$, a seven-residue fragment of the Alzheimer's β-amyloid peptide, and structural characterization by solid state NMR" Biochemistry, vol. 39, pp. 13748-59 (2000).

Simmons, L. "Secondary Structure of amyloid β peptide correlates with neurotoxic activity *In Vitro*" Molecular Pharmacology, vol. 45, pp. 373-9 (1994).

Wood, A. et al. "Prolines and amyloidogenicity in fragments of the Alzheimer's peptide β/A4" Biochemistry, vol. 34 pp. 724-30 (1995).

Xu, S. and Gaskin, F. "Increased incidence of anti-β-amyloid autoantibodies secreted by Epstein-Barr virus transformed B cell lines from patients with Alzheimer's disease" Mechanisms of Ageing and Development, vol. 94, pp. 213-22 (1997).

Soto, C. et al. "The α-helical to β-strand transition in the amino-terminal fragment of the amyloid β-peptide modulates amyloid formation" J. Biol. Biol. Chem, vol. 270, No. 7, pp. 3063-67 (1995).

Tjernberg, L. et al. "A molecular model for Alzheimer amyloid β-peptide fibril formation" J. Biol. Biol. Chem, vol. 274, No. 18, pp. 12619-25 (1999).

Hilbich, C. et al. "Substitutions of hydrophobic amino acid reduce the amyloidogenicity of Alzheimer's disease βA4 peptides" J. Mol. Biol., vol. 228, pp. 460-73 (1992).

Hilbich, C. et al. "Human and rodent sequence analogs of Alzheimer's amyloid βA4 share similar properties and can be solubized in buffers of pH 7.4" Eur. J. Biochem., vol. 201, pp. 61-69 (1991).

Hilbich, C. et al. "Aggregation and secondary structure of synthetic amyloid βA4 peptides of Alzheimer's disease" J. Mol. Biol., vol. 218, pp. 149-163 (1991).

Levitt M, "Molecular dynamics of native protein," *J Mol Biol*, 168:595-620 (1983).

Queen C et al., "A humanized antibody that binds to the interleukin 2 receptor," *Proc Natl Acad Sci USA*, 8610029-10033 (1989).

Burdick D et al., "Assembly and aggregation properties of synthetic Alzheimer's A4/β amyloid peptide analogs," *J Biol Chem*, 267:546-55 (1992).

Co MS et al., "Chimeric and humanized antibodies with specificity for the CD33 antigen," *J Immunol*, 148:1149-1154 (1992).

Ghiso J et al., "Epitope map of two polyclonal antibodies that recognize amyloid lesions in patients with Alzheimer's disease," *Biochem J*, 282 (pt 2):517-522 (1992).

Haass C et al., "Amyloid beta-peptide is produced by cultured cells during normal metabolism," *Nature*, 359:322-5 (1992).

Seubert P et al., "Isolation and quantification of soluble Alzheimer's β peptide from biological fluids," *Nature*, 359:325-327 (1992).

Gaskin F et al., "Human antibodies reactive with beta-amyloid protein in Alzheimer's disease," *J Exp Med*, 177(4):1181-1186 (1993).

Flood JF et al., "An amyloid β -protein fragment, A β [12-28], equipotently impairs post-training memory processing when injected into different limbic system structures," *Brain Res*, 663(2):271-276 (1994).

Koudinov A et al., "The soluble form of Alzheimer's amyloid beta protein is complexed to high density lipoprotein 3 and very high density lipoprotein in normal human plasma," *Biochem & Biophysic Res Comm*, 205:1164-1171 (1994).

Schwarzman AL et al., "Transthyretin sequesters amyloid β protein and prevents amyloid formation," *Proc Natl Acad Sci*, 91:8368-8372, (1994).

Tabaton M et al., "Soluble amyloid β-protein is a marker of Alzheimer amyloid in brain but not in cerebrospinal fluid," *Biochem and Biophysi Res Comm*, 200(3):1598-1603 (1994).

Walker LC et al., "Labeling of cerebral amyloid in vivo with a monoclonal antibody," *J Neuropathol Exp Neurol*, 53(4):377-383 (1994).

Wisniewski T et al., "Alzheimer's disease and soluble A beta," *Neurobiol Aging*, 15(2):143-52 Review (1994).

DeMattos RB et al., "Peripheral antio-Aβ antibody alters CNS and plasma Aβ clearance and decreases Aβ burden in a mouse model of Alzheimer's disease," *Proc Natl Acad Sci USA*, 98(15):8850-8855 (1996).

Giulian D et al., "Specific domains of β-amyloid from Alzheimer plaque elicit neuron killing in human microglia," *J Neurosci*, 16 (19):6021-6037 (1996).

Hanan E et al., "Inhibitory effect of monoclonal antibodies on Alzheimer's βamyloid peptide aggregation," *Int J Exp Clin Invest*, 3:130-133 (1996).

Solomon B et al., "Monoclonal antibodies inhibit *in vitro* fibrillar aggregation of the Alzheimer beta-amyloid peptide," *Proc Natl Acad Sci USA*, 93(1):452-5 (1996).

Teller JK et al., "Presence of soluble amyloid β-peptide precedes amyloid plaque formation in Down's syndrome," *Nature Medicine*, 2(1)93-95 (1996).

Tjernberg LO et al., "Arrest of beta-amyloid fibril formation by a pentapeptide ligand," *J Biol Chem*, 271(15):8545-8548 (1996).

Winter G et al., "Humanized antibodies" *Immunology Today*, 14(6):243-246 (1996).

Solomon B et al., "Disaggregation of Alzheimer beta-amyloid by site-directed mAb," *Proc Natl Acad Sci USA*, 94(8):4109-4112 (1997).

El-Agnaf OM et al., "The influence of the central region containing residues 19-25 on the aggregation properties and secondary structure of Alzheimer's beta-amyloid peptide," *Eur J Biochem*, 256(3):560-569.

He X-Y et al., "Humanization and pharmacokinetics of a monoclonal antibody with specificity for bothe E- and P- selection," *J Immunol*, 160:1029-1035 (1998).

Lambert MP et al., "Diffusible, nonfibrillar ligands derived from Aβ1-42 are potent central nervous system neurotoxins," *Proc Natl Acad Sci*, 95:6448-6453 (1998).

Solomon B et al., "The amino terminus of the β-amyloid peptide contains an essential epitope for maintaining its solubility," *Progress in Alzheimer's and Parkinson's Diseases*, 205-211 (1998).

Soto C et al., "β-sheet breaker peptides inhibit fibrillogenesis in a rat brain model of amyloidosis: Implications of Alzheimer'therapy," *Nature Medicine*, 4(7):822-826 (1998).

Blass JP, "Immunologic treatment of Alzheimer's disease," *NEJM*, 341:1694-1695 (1999).

Kuo YM et al., "High levels of circulating Abeta42 are sequestered by plasma proteins in Alzheimer's disease," *Biochem Biophys Res Commun*, 257(3):787-791 (1999).

McLean C et al., "Soluble pool of Aβ amyloid as a determinant of severity of neurodegeneration in Alzheimer's disease," *Amer Neurological Assoc*, 46:860-866 (1999).

Schenk D et al., "Immunization with amyloid-β attenuates Alzheimer-disease-like pathology in the PDAPP mouse," *Nature*, 400:173-177 (1999).

St. George-Hyslop P et al., "Antibody clears senile plaques" *Nature*, 400:116-117 (1999).

Wang J et al., "The levels of soluble versus insoluble brain Aβ distinguish Alzheimer's disease from normal and pathologic aging," *Experimental Neurology*, 158:328-337 (1999).

Bard F et al., "Peripherally administered antibodies against amyloid beta-peptide enter the central nervous system and reduce pathology in a mouse model of Alzheimer disease," *Nat Med*, 6(8):916-919 (2000).

Games D et al., "Prevention and reduction of AD-type pathology in PDAPP mice immunized with $A\beta_{1-42}$," *Annals of NY Acad Sci*, 920:274-284 (2000).

Levy A et al., "Immunization for Alzheimer's disease: A shot in the arm or a whiff?" *American Neurological Assoc*, 48:553-554 (2000).

Janus C et al., "Aβ peptide immunization reduces behavioural impairment and plaques in a model of Alzheimer's disease," *Nature*, 408:979-982 (2000).

Morgan D et al., "Aβ peptide vaccination prevents memory loss in an animal model of Alzheimer's disease," *Nature*, 408:982-985 (2000).

Naslund J et al., "Correlation between elevated levels of amyloid β peptide in the brain and cognitive decline," *J Am Med Assoc*, 283:1571 (2000).

Zlokovic BV et al., "Clearance of amyloid β-peptide from brain: transport or metabolism?" *Nature Medicine*, 6(7):718-719 (2000).

Arendash GW et al., "Behavioral assessment of Alzheimer's transgenic mice following long-term Aβ vaccination: Task specificity and correlations between Aβ deposition and spatial memory," *DNA and Cell Biology*, 20(11):737-744 (2001).

Bacskai BJ et al., "Imaging of amyloid-β deposits in brains of living mice permits direct observation of clearance of plaques with immunotherapy," *Nature Medicine*, 7(3):369-372 (2001).

DeMattos RB et al., "Peripheral anti-Aβ antibody alters CNS and plasma Aβ clearance and decreases brain Aβ burden in a mouse model of Alzheimer's disease," *PNAS*, 98(15):8850-8855 (2001).

Dickey CA et al., "Duration and specificity of humoral immune responses in mice vaccinated with the Alzheimer's disease-associated β-amyloid 1-42 peptide," *DNA and Cell Biology*, 20(11):723-729 (2001).

Esiri MM et al., "Is an effective immune intervention for Alzheimer's disease in prospect?" *Trends Pharmacol Sci*, 22(1):2-3 (2001).

Haass C et al., "Protofibrils, the unifying toxic molecule of neurodegenerative disorders?" *Nature Neuroscience*, 4(9):859-860 (2001).

Klein WL et al., "Targeting small Aβ oligomers: the solution to an Alzheimer's disease conundrum?" *Trends in Neurosciences*, 24(4):219-224 (2001).

Lambert MP et al., "Vaccination with soluble Aβ oligomers generates toxicity-neutralizing antibodies," *J Neurochem*, 79:595-605 (2001).

Lee VM-Y et al., "Aβ immunization: Moving Aβ peptide from brain to blood," *PNAS*, 98(16):8931-8932 (2001).

Poduslo JF et al., "Permeability of proteins at the blood-brain barrier in the normal adult mouse and double transgenic mouse model of Alzheimer's disease," *Neurobiol Dis*, 8(4):555-67 (2001).

Town T et al., "Characterization of murine immunoglobulin G antibodies against human amyloid-$\beta_{1-42}$," *Neurosci Lett*, 307:101-104 (2001).

DeMattos RB et al., "Plaque-associated disruption of CSF and plasma amyloid-β (Aβ) equilibrium in a mouse model of Alzheimer's disease," *J Neurochem*, 81:229-236, (2002).

Kotilinek LA et al., "Reversible memory loss in a mouse transgenic model of Alzheimer's disease," *J Neurosci*, 22(15):6331-6335 (2002).

Wang H-W et al., "Soluble oligomers of β amyloid (1-42) inhibit long-term potentiation but not long-term depression in rate dentate gyrus," *Brain Research*, 924:133-140 (2002).

Pillot, T. et al. "Fusogenic Properites of the C-terminal Domain of the Alzheimer β-Amyloid Peptide" J. Biol Chem., vol. 271, No. 24, pp. 28757-65 (1996).

* cited by examiner

```
619 ACGCGTCCACCATGAAGTTGCCTGTTAGGCTGTTGGTGCTGATGTTCTGGATTCCTGCTTCCAGGTGTGATGTTGTGATG
              M   K   L   P   V   R   L   L   V   L   M   F   W   I   P   A   S   R   C   D   V   V   M

699 ACCCAGAGCCCACTCTCCCTGCCTGTCACCCTTGGACAACCAGCCTCCATCTCTTGCAGATCTAGTCAGAGCCTTATATA
       T   Q   S   P   L   S   L   P   V   T   L   G   Q   P   A   S   I   S   C   R   S   S   Q   S   L   I   Y

779 TAGTGATGGAAACGCCTATTTACATTGGTTCTTGCAGAAGCCAGGCCAGTCTCCAAGGCTCCTGATCTACAAAGTTTCCA
       S   D   G   N   A   Y   L   H   W   F   L   Q   K   P   G   Q   S   P   R   L   L   I   Y   K   V   S   N

859 ACCGATTTTCTGGGGTCCCAGACAGGTTCAGTGGCAGTGGATCTGGGACAGATTTCACACTCAAGATCAGCAGAGTGGAG
       R   F   S   G   V   P   D   R   F   S   G   S   G   S   G   T   D   F   T   L   K   I   S   R   V   E

939 GCCGAGGATGTGGGAGTTTATTACTGTTCTCAAAGTACACATGTTCCGTGGACGTTCGGTCAAGGCACCAAGGTGGAAAT
       A   E   D   V   G   V   Y   Y   C   S   Q   S   T   H   V   P   W   T   F   G   Q   G   T   K   V   E   I

1019 CAAACGTGAGTAGAATTTAATCTAGAAATTCTAAACTCTGAGGGGGTCGGATGACGTGGCCATTCTTTGCCTAAAGCATT
       K   R

1099 GAGTTTACTGCAAGGTCAGAAAAGCATGCAAAGCCCTCAGAATGGCTGCAAAGAGCTCCAACAAAACAATTTAGAACTTT
1179 ATTAAGGAATAGGGGGAAGCTAGGAAGAAACTCAAAACATCAAGATTTTAAATACGCTTCTTGGTCTCCTTGCTATAATT
1259 ATCTGGGATAAGCATGCTGTTTTCTGTCTGTCCCTAACATGCCCTGTGATTATCCGCAAACAACACACCCAAGGGCAGAA
1339 CTTTGTTACTTAAACACCATCCTGTTTGCTTCTTTCCTCAGGAACTGTGGCTGCACCATCTGTCTTCATCTTCCCGCCAT
                                                        T   V   A   A   P   S   V   F   I   F   P   P   S

1419 CTGATGAGCAGTTGAAATCTGGAACTGCCTCTGTTGTGTGCCTGCTGAATAACTTCTATCCCAGAGAGGCCAAAGTACAG
       D   E   Q   L   K   S   G   T   A   S   V   V   C   L   L   N   N   F   Y   P   R   E   A   K   V   Q   W

1499 TGGAAGGTGGATAACGCCCTCCAATCGGGTAACTCCCAGGAGAGTGTCACAGAGCAGGACAGCAAGGACAGCACCTACAG
       K   V   D   N   A   L   Q   S   G   N   S   Q   E   S   V   T   E   Q   D   S   K   D   S   T   Y   S   L

1579 CCTCAGCAGCACCCTGACGCTGAGCAAAGCAGACTACGAGAAACACAAAGTCTACGCCTGCGAAGTCACCCATCAGGGCC
       S   S   T   L   T   L   S   K   A   D   Y   E   K   H   K   V   Y   A   C   E   V   T   H   Q   G   L

1659 TGAGCTCGCCCGTCACAAAGAGCTTCAACAGGGGAGAGTGTTAGAGGGAGAAGTGCCCCCACCTGCTCCTCAGTTCCAGC
       S   S   P   V   T   K   S   F   N   R   G   E   C   *

1739 CTGACCCCCTCCCATCCTTTGGCCTCTGACCCTTTTTCCACAGGGGACCTACCCCTATTGCGGTCCTCCAGCTCATCTTT
1819 CACCTCACCCCCCTCCTCCTCCTTGGCTTTAATTATGCTAATGTTGGAGGAGAATGAATAAATAAAGTGAATCTTTGCAC
1899 CTGTGGTTTCTCTCTTTCCTCATTTAATAATTATTATCTGTTGTTTTACCAACTACTCAATTTCTCTTATAAGGGACTAA
1979 ATATGTAGTCATCCTAAGGCGCATAACCATTTATAAAAATCATCCTTCATTCTATTTTACCCTATCATCCTCTGCAAGAC
2059 AGTCCTCCCTCAAACCCACAAGCCTTCTGTCCTCACAGTCCCCTGGGCCATGGTAGGAGAGACTTGCTTCCTTGTTTTCC
2139 CCTCCTCAGCAAGCCCTCATAGTCCTTTTTAAGGGTGACAGGTCTTACAGTCATATATCCTTTGATTCAATTCCCTGAGA
2219 ATCAACCAAAGCAAATTTTTCAAAAGAAGAAACCTGCTATAAAGAGAATCATTCATTGCAACATGATATAAAATAACAAC
2299 ACAATAAAAGCAATTAAATAAACAAACAATAGGGAAATGTTTAAGTTCATCATGGTACTTAGACTTAATGGAATGTCATG
2379 CCTTATTTACATTTTTAAACAGGTACTGAGGGACTCCTGTCTGCCAAGGGCCGTATTGAGTACTTTCCACAACCTAATTT
2459 AATCCACACTATACTGTGAGATTAAAAACATTCATTAAAATGTTGCAAAGGTTCTATAAAGCTGAGAGACAAATATATTC
2539 TATAACTCAGCAATCCCACTTCTAGGATCC
```

FIG 4

```
 619 ACGCGTCCACCATGAATTTCGGGCTCAGCTTGATTTTCCTTGTCCTTGTTTTAAAAGGTGTCCTGTGTGAAGTGCAGCTG
              M  N  F  G  L  S  L  I  F  L  V  L  V  L  K  G  V  L  C  E  V  Q  L

699 GTGGAGTCTGGGGGAGGTTTAGTGCAGCCTGGAGGGTCCCTGAGACTCTCCTGTGCAGCCTCTGGATTCACTTTTAGTAG
     V  E  S  G  G  G  L  V  Q  P  G  G  S  L  R  L  S  C  A  A  S  G  F  T  F  S  R

779 GTATTCCATGTCTTGGGTTCGCCAGGCTCCAGGCAAGGGCCTGGAATTGGTCGCACAAATTAATAGTGTTGGTAATAGCA
     Y  S  M  S  W  V  R  Q  A  P  G  K  G  L  E  L  V  A  Q  I  N  S  V  G  N  S

859 CCTACTATCCAGACACTGTAAAGGGCCGATTCACCATCTCCAGAGACAATGCCAAGAACACCCTGTACCTGCAAATGAAC
     T  Y  Y  P  D  T  V  K  G  R  F  T  I  S  R  D  N  A  K  N  T  L  Y  L  Q  M  N

939 TCCCTGAGGGCTGAAGACACGGCCGTGTATTACTGTGCAAGCGGAGACTACTGGGGCCAAGGCACCCTGGTGACAGTCTC
     S  L  R  A  E  D  T  A  V  Y  Y  C  A  S  G  D  Y  W  G  Q  G  T  L  V  T  V  S

1019 CTCAGGTGAGTCCTCACAACCTCTAGAGCTTTCTGGGGCAGGCCAGGCCTGACCTTGGCTTTGGGGCAGGGAGGGCGCTA
     S

1099 AGGTGAGGCAGGTGCCGCCAGCCAGGTGCACACCCAATGCCCATGAGCCCAGACACTGGACGCTGAACCTCGCGGACAGT
1179 TAAGAACCCAGGGGCCTCTGCGCCCTGGGCCCAGCTCTGTCCCACACCGCGGTCACATGGCACCACCTCTCTTGCAGCCT
                                                                                   A

1259 CCACCAAGGGCCCATCGGTCTTCCCCCTGGCACCCTCCTCCAAGAGCACCTCTGGGGGCACAGCGGCCCTGGGCTGCCTG
     S  T  K  G  P  S  V  F  P  L  A  P  S  S  K  S  T  S  G  G  T  A  A  L  G  C  L

1339 GTCAAGGACTACTTCCCCGAACCGGTGACGGTGTCGTGGAACTCAGGCGCCCTGACCAGCGGCGTGCACACCTTCCCGGC
     V  K  D  Y  F  P  E  P  V  T  V  S  W  N  S  G  A  L  T  S  G  V  H  T  F  P  A

1419 TGTCCTACAGTCCTCAGGACTCTACTCCCTCAGCAGCGTGGTGACCGTGCCCTCCAGCAGCTTGGGCACCCAGACCTACA
     V  L  Q  S  S  G  L  Y  S  L  S  S  V  V  T  V  P  S  S  S  L  G  T  Q  T  Y

1499 TCTGCAACGTGAATCACAAGCCCAGCAACACCAAGGTGGACAAGAAAGTTGGTGAGAGGCCACCACAGGGAGGGAGGGTG
     I  C  N  V  N  H  K  P  S  N  T  K  V  D  K  K  V

1579 TCTGCTGGAAGCCAGGCTCAGCGCTCCTGCCTGGACGCATCCCGGCTATGCAGCCCCAGTCCAGGGCAGCAAGGCAGGCC
1659 CCGTCTGCCCTCTTCACCCGCGAGCCCTCTGCCCGCCCCACTCATGCTCAGGGAGAGGGTCTTCTGGCTTTTTCCCCAGGCT
1739 CTGGGCAGCCACAGGCTAGGTGCCCCTAACCCAGGCCCTGCACACAAAGGGCAGGTGCTGGGCTCAGACCTGCCAAGAG
1819 CCATATCCGGCAGGACCCTGCCCCTGACCTAAGCCCACCCCAAAGGCCAAACTCTCCACTCCCTCAGCTCGGACACCTTC
1899 TCTCCTCCCAGATTCCAGTAACTCCCAATCTTCTCTCTGCAGAGCCCAAATCTTGTGACAAAACTCACACATGCCCACCG
                                                   E  P  K  S  C  D  K  T  H  T  C  P  P

1979 TGCCCAGGTAAGCCAGCCCAGGCCTCGCCCTCCAGCTCAAGGCGGGACAGGTGCCCTAGAGTAGCCTGCATCCAGGGACA
     C  P

2059 GGCCCCAGCCGGGTGCTGACACGTCCACCTCCATCTCTTCCTCAGCACCTGAACTCCTGGGGGGACCGTCAGTCTTCCTC
                                                    A  P  E  L  L  G  G  P  S  V  F  L

2139 TTCCCCCCAAAACCCAAGGACACCCTCATGATCTCCCGGACCCCTGAGGTCACATGCGTGGTGGTGGACGTGAGCCACGA
     F  P  P  K  P  K  D  T  L  M  I  S  R  T  P  E  V  T  C  V  V  V  D  V  S  H  E

2219 AGACCCTGAGGTCAAGTTCAACTGGTACGTGGACGGCGTGGAGGTGCATAATGCCAAGACAAAGCCGCGGGAGGAGCAGT
     D  P  E  V  K  F  N  W  Y  V  D  G  V  E  V  H  N  A  K  T  K  P  R  E  E  Q

2299 ACAACAGCACGTACCGTGTGGTCAGCGTCCTCACCGTCCTGCACCAGGACTGGCTGAATGGCAAGGAGTACAAGTGCAAG
     Y  N  S  T  Y  R  V  V  S  V  L  T  V  L  H  Q  D  W  L  N  G  K  E  Y  K  C  K

2379 GTCTCCAACAAAGCCCTCCCAGCCCCCATCGAGAAAACCATCTCCAAAGCCAAAGGTGGGACCCGTGGGGTGCCAGGGCC
     V  S  N  K  A  L  P  A  P  I  E  K  T  I  S  K  A  K

2459 ACATGGACAGAGGCCGGCTCGGCCCACCCTCTGCCCTGAGAGTGACCGCTGTACCAACCTCTGTCCCTACAGGGCAGCCC
                                                                                   G  Q  P

2539 CGAGAACCACAGGTGTACACCCTGCCCCCATCCCGGGATGAGCTGACCAAGAACCAGGTCAGCCTGACCTGCCTGGTCAA
     R  E  P  Q  V  Y  T  L  P  P  S  R  D  E  L  T  K  N  Q  V  S  L  T  C  L  V  K

2619 AGGCTTCTATCCCAGCGACATCGCCGTGGAGTGGGAGAGCAATGGGCAGCCGGAGAACAACTACAAGACCACGCCTCCCG

G  F  Y  P  S  D  I  A  V  E  W  E  S  N  G  Q  P  E  N  N  Y  K  T  T  P  P

2699 TGCTGGACTCCGACGGCTCCTTCTTCCTCTACAGCAAGCTCACCGTGGACAAGAGCAGGTGGCAGCAGGGGAACGTCTTC
     V  L  D  S  D  G  S  F  F  L  Y  S  K  L  T  V  D  K  S  R  W  Q  Q  G  N  V  F

2779 TCATGCTCCGTGATGCATGAGGCTCTGCACAACCACTACACGCAGAAGAGCCTCTCCCTGTCTCCGGGTAAATGAGTGCG
     S  C  S  V  M  H  E  A  L  H  N  H  Y  T  Q  K  S  L  S  L  S  P  G  K  •

2859 ACGGCCGGCAAGCCCCCGCTCCCCGGGCTCTCGCGGTCGCACGAGGATGCTTGGCACGTACCCCCTGTACATACTTCCCG
2939 GGCGCCCAGCATGGAAATAAAGCACCCAGCGCTGCCCTGGGCCCCTGCGAGACTGTGATGGTTCTTTCCACGGGTCAGGC
3019 CGAGTCTGAGGCCTGAGTGGCATGACGGAGGCAGAGCGGGTCCCACTGTCCCCACACTGGCCCAGGCTGTGCAGGTGTGC
3099 CTGGGCCGCCTAGGGTGGGGCTCAGCCAGGGGCTGCCCTCGGCAGGGTGGGGGATTTGCCAGCGTGGCCCTCCCTCCAGC
3179 AGCACCTGCCCTGGGCTGGGCCACGGGAAGCCCTAGGAGCCCCTGGGGACAGACACACAGCCCCTGCCTCTGTAGGACAC
3259 TGTCCTGTTCTGTGAGCGCCCTGTCCTCCGACCTCCATGCCCACTCGGGGGCATGCCTAGTCCATGTGCGTAGGGACAGG
3339 CCCTCCCTCACCCATCTACCCCCACGGCACTAACCCCTGGCTGCCCTGCCCAGCCTCGCACCCGCATGGGGACACAACCG
3419 ACTCCGGGGACATGCACTCTCCGGCCCTGTGGACGGACTGGTGCAGATGCCCACACACACACTCAGCCCAGACCCGTTCA
3499 ACAAACCCCGCACTCGAGGTTGGCCGGCCACACGGCCACCACACACACACGTGCACGCCTCACACACGGAGCCTCACCCGG
3579 GCGAACTGCACAGCACCCAGACCAGAGCAAGGTCCTCGCACACGTGAACACTCCTCGGACACAGGCCCCACGAGCCCCA
3659 CGCGGCACCTCAAGGCCCACGAGCCTCTCGGCAGCTTCTCCACATGCTGACCTGCTCAGACAAACCCAGCCCTCCTCTCA
3739 CAAGGGTGCCCCTGCAGCCGCCACACACACACAGGGGATCACACACCACGTCACGTCCCTGGCCCTGGCCCACTTCCAG
3819 TGCCGCCCTTCCCTGCAGGATCC
```

FIG 5

SEQUENCE LISTING

<160> NUMBER OF SEQ ID NOS: 16

<210> SEQ ID NO 1
<211> LENGTH: 16
<212> TYPE: PRT
<213> ORGANISM: Mus sp.

<400> SEQUENCE: 1

Arg Ser Ser Gln Ser Leu Ile Tyr Ser Asp Gly Asn Ala Tyr Leu His
1               5                   10                  15

<210> SEQ ID NO 2
<211> LENGTH: 7
<212> TYPE: PRT
<213> ORGANISM: Mus sp.

<400> SEQUENCE: 2

Lys Val Ser Asn Arg Phe Ser
1               5

<210> SEQ ID NO 3
<211> LENGTH: 9
<212> TYPE: PRT
<213> ORGANISM: Mus sp.

<400> SEQUENCE: 3

Ser Gln Ser Thr His Val Pro Trp Thr
1               5

<210> SEQ ID NO 4
<211> LENGTH: 5
<212> TYPE: PRT
<213> ORGANISM: Mus sp.

<400> SEQUENCE: 4

Arg Tyr Ser Met Ser
1               5

<210> SEQ ID NO 5
<211> LENGTH: 17
<212> TYPE: PRT
<213> ORGANISM: Mus sp.

<400> SEQUENCE: 5

Gln Ile Asn Ser Val Gly Asn Ser Thr Tyr Tyr Pro Asp Thr Val Lys
1               5                   10                  15

Gly

<210> SEQ ID NO 6
<211> LENGTH: 3
<212> TYPE: PRT
<213> ORGANISM: Mus sp.

<400> SEQUENCE: 6

Gly Asp Tyr
1

<210> SEQ ID NO 7
<211> LENGTH: 113
<212> TYPE: PRT
<213> ORGANISM: Artificial sequence
<220> FEATURE:
<223> OTHER INFORMATION: Humanized antibodies

```
<220> FEATURE:
<221> NAME/KEY: MISC_FEATURE
<222> LOCATION: (2)..(2)
<223> OTHER INFORMATION: Xaa at position 2 is Val or Ile
<220> FEATURE:
<221> NAME/KEY: MISC_FEATURE
<222> LOCATION: (7)..(7)
<223> OTHER INFORMATION: Xaa at position 7 is Ser or Thr
<220> FEATURE:
<221> NAME/KEY: MISC_FEATURE
<222> LOCATION: (14)..(14)
<223> OTHER INFORMATION: Xaa at position 14 is Thr or Ser
<220> FEATURE:
<221> NAME/KEY: MISC_FEATURE
<222> LOCATION: (15)..(15)
<223> OTHER INFORMATION: Xaa at position 15 is Leu or Pro
<220> FEATURE:
<221> NAME/KEY: MISC_FEATURE
<222> LOCATION: (30)..(30)
<223> OTHER INFORMATION: Xaa at position 30 is Ile or Val
<220> FEATURE:
<221> NAME/KEY: MISC_FEATURE
<222> LOCATION: (50)..(50)
<223> OTHER INFORMATION: Xaa at position 50 is Arg, Gln, or Lys
<220> FEATURE:
<221> NAME/KEY: MISC_FEATURE
<222> LOCATION: (88)..(88)
<223> OTHER INFORMATION: Xaa at position 88 is Val or Leu
<220> FEATURE:
<221> NAME/KEY: MISC_FEATURE
<222> LOCATION: (105)..(105)
<223> OTHER INFORMATION: Xaa at position 105 is Gln or Gly
<220> FEATURE:
<221> NAME/KEY: MISC_FEATURE
<222> LOCATION: (108)..(108)
<223> OTHER INFORMATION: Xaa at position 108 is Lys or Arg
<220> FEATURE:
<221> NAME/KEY: MISC_FEATURE
<222> LOCATION: (109)..(109)
<223> OTHER INFORMATION: Xaa at position 109 is Val or Leu

<400> SEQUENCE: 7

Asp Xaa Val Met Thr Gln Xaa Pro Leu Ser Leu Pro Val Xaa Xaa Gly
 1               5                  10                  15

Gln Pro Ala Ser Ile Ser Cys Arg Ser Ser Gln Ser Leu Xaa Tyr Ser
                20                  25                  30

Asp Gly Asn Ala Tyr Leu His Trp Phe Leu Gln Lys Pro Gly Gln Ser
            35                  40                  45

Pro Xaa Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Ser Gln Ser
                85                  90                  95

Thr His Val Pro Trp Thr Phe Gly Xaa Gly Thr Xaa Xaa Glu Ile Lys
            100                 105                 110

Arg

<210> SEQ ID NO 8
<211> LENGTH: 112
<212> TYPE: PRT
<213> ORGANISM: Artificial sequence
<220> FEATURE:
<223> OTHER INFORMATION: Humanized antibodies
<220> FEATURE:
<221> NAME/KEY: MISC_FEATURE
<222> LOCATION: (1)..(1)
<223> OTHER INFORMATION: Xaa at position 1 is Glu or Gln
<220> FEATURE:
<221> NAME/KEY: MISC_FEATURE
```

```
<222> LOCATION: (7)..(7)
<223> OTHER INFORMATION: Xaa at position 7 is Ser or Leu
<220> FEATURE:
<221> NAME/KEY: MISC_FEATURE
<222> LOCATION: (46)..(46)
<223> OTHER INFORMATION: Xaa at position 46 is Glu, Val, Asp or Ser
<220> FEATURE:
<221> NAME/KEY: MISC_FEATURE
<222> LOCATION: (63)..(63)
<223> OTHER INFORMATION: Xaa at position 63 is Thr or Ser
<220> FEATURE:
<221> NAME/KEY: MISC_FEATURE
<222> LOCATION: (75)..(75)
<223> OTHER INFORMATION: Xaa at position 75 is Ala, Ser, Val or Thr
<220> FEATURE:
<221> NAME/KEY: MISC_FEATURE
<222> LOCATION: (76)..(76)
<223> OTHER INFORMATION: Xaa at position 76 is Lys or Arg
<220> FEATURE:
<221> NAME/KEY: MISC_FEATURE
<222> LOCATION: (89)..(89)
<223> OTHER INFORMATION: Xaa at position 89 is Glu or Asp
<220> FEATURE:
<221> NAME/KEY: MISC_FEATURE
<222> LOCATION: (107)..(107)
<223> OTHER INFORMATION: Xaa at position 107 is Leu or Thr

<400> SEQUENCE: 8

Xaa Val Gln Leu Val Glu Xaa Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Xaa Leu Val
        35                  40                  45

Ala Gln Ile Asn Ser Val Gly Asn Ser Thr Tyr Tyr Pro Asp Xaa Val
    50                  55                  60

Lys Gly Arg Phe Thr Ile Ser Arg Asp Asn Xaa Xaa Asn Thr Leu Tyr
65                  70                  75                  80

Leu Gln Met Asn Ser Leu Arg Ala Xaa Asp Thr Ala Val Tyr Tyr Cys
                85                  90                  95

Ala Ser Gly Asp Tyr Trp Gly Gln Gly Thr Xaa Val Thr Val Ser Ser
            100                 105                 110

<210> SEQ ID NO 9
<211> LENGTH: 113
<212> TYPE: PRT
<213> ORGANISM: Artificial sequence
<220> FEATURE:
<223> OTHER INFORMATION: Humanized antibodies

<400> SEQUENCE: 9

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Ile Tyr Ser
            20                  25                  30

Asp Gly Asn Ala Tyr Leu His Trp Phe Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95
```

```
Thr His Val Pro Trp Thr Phe Gly Gln Gly Thr Lys Val Glu Ile Lys
                100                 105                 110
Arg

<210> SEQ ID NO 10
<211> LENGTH: 112
<212> TYPE: PRT
<213> ORGANISM: Artificial sequence
<220> FEATURE:
<223> OTHER INFORMATION: Humanized antibodies

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Glu Leu Val
        35                  40                  45

Ala Gln Ile Asn Ser Val Gly Asn Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Leu Val Thr Val Ser Ser
            100                 105                 110

<210> SEQ ID NO 11
<211> LENGTH: 219
<212> TYPE: PRT
<213> ORGANISM: Artificial sequence
<220> FEATURE:
<223> OTHER INFORMATION: Humanized antibodies

<400> SEQUENCE: 11

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Ile Tyr Ser
            20                  25                  30

Asp Gly Asn Ala Tyr Leu His Trp Phe Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140
```

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
    210                 215

<210> SEQ ID NO 12
<211> LENGTH: 442
<212> TYPE: PRT
<213> ORGANISM: Artificial sequence
<220> FEATURE:
<223> OTHER INFORMATION: Humanized antibodies

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Glu Leu Val
        35                  40                  45

Ala Gln Ile Asn Ser Val Gly Asn Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
            165                 170                 175

Leu Ser Ser Val Val Thr Val Pro Ser Ser Ser Leu Gly Thr Gln Thr
        180                 185                 190

Tyr Ile Cys Asn Val Asn His Lys Pro Ser Asn Thr Lys Val Asp Lys
    195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285
```

-continued

```
Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440
```

<210> SEQ ID NO 13
<211> LENGTH: 46
<212> TYPE: DNA
<213> ORGANISM: Synthetic nucleotides

<400> SEQUENCE: 13
tatagagctc aagcttggat ggtgggaaga tggatacagt tggtgc                46

<210> SEQ ID NO 14
<211> LENGTH: 50
<212> TYPE: DNA
<213> ORGANISM: Synthetic nucleotides

<400> SEQUENCE: 14
tatagagctc aagcttccag tggatagach gatggggstg tygttttggc            50

<210> SEQ ID NO 15
<211> LENGTH: 16
<212> TYPE: PRT
<213> ORGANISM: Artificial sequence
<220> FEATURE:
<223> OTHER INFORMATION: Humanized antibodies

<400> SEQUENCE: 15

```
Arg Ser Ser Gln Ser Leu Val Tyr Ser Asp Gly Asn Ala Tyr Leu His
1               5                   10                  15
```

<210> SEQ ID NO 16
<211> LENGTH: 17
<212> TYPE: PRT
<213> ORGANISM: Artificial Sequence
<220> FEATURE:
<223> OTHER INFORMATION: Humanized antibodies

<400> SEQUENCE: 16

```
Gln Ile Asn Ser Val Gly Asn Ser Thr Tyr Tyr Pro Asp Ser Val Lys
1               5                   10                  15
Gly
```

HUMANIZED ANTIBODIES THAT SEQUESTER ABETA PEPTIDE

CROSS-REFERENCE TO RELATED APPLICATIONS

This application is a continuation of PCT patent application PCT/US01/06191, filed Feb. 26, 2001, which was published in English and designated the United States and which claims the priority of U.S. provisional applications 60/184,601, filed Feb. 24, 2000, 60/256,465 filed Dec. 8, 2000, and 60/254,498, filed Dec. 8, 2000. The contents of each of these applications are incorporated herein by reference.

TECHNICAL FIELD

The invention relates to humanized antibodies that bind to an epitope between amino acids 13 and 28 of the Aβ peptide and to preventive and therapeutic treatment of conditions associated with beta amyloid, such as Alzheimer's disease, Down's syndrome, and cerebral amyloid angiopathey. More specifically, it concerns use of humanized monoclonal antibodies to sequester amyloid beta (Aβ) peptide in plasma, brain, and cerebrospinal fluid to prevent accumulation or to reverse deposition of the Aβ peptide within the brain and in the cerebrovasculature and to improve cognition.

BACKGROUND ART

A number of symptomologies which result in cognitive deficits, stroke, brain hemorrhage, and general mental debilitation appear to be associated with neuritic and cerebrovascular plaques in the brain containing the amyloid beta peptide (Aβ). Among these conditions are both pre-clinical and clinical Alzheimer's disease, Down's syndrome, and pre-clinical and clinical cerebral amyloid angiopathy (CAA). The amyloid plaques are formed from amyloid beta peptides. These peptides circulate in the blood and in the cerebrospinal fluid (CSF), typically in complexed form with lipoproteins. The Aβ peptide in circulating form is composed of 39–43 amino acids (mostly 40 or 42 amino acids) resulting from the cleavage of a common precursor protein, amyloid precursor protein, often designated APP. Some forms of soluble Aβ are themselves neurotoxic and may determine the severity of neurodegeneration and/or cognitive decline (McLean, C. A., et al., *Ann. Neurol.* (1999) 46:860–866; Lambert, M. P., et al. (1998) 95:6448–6453; Naslund, J., *J. Am. Med. Assoc.* (2000) 283:1571).

Evidence suggests that Aβ can be transported back and forth between brain and the blood (Ghersi-Egea, J-F., et al., *J. Neurochem.* (1996) 67:880–883; Zlokovic, B. V., et al, *Biochem. Biophys. Res. Comm.* (1993) 67:1034–1040; Shibata M, et al., *J. Clin. Invest.* (2000) 106:1489–1499). Further Aβ in plaques is in an equilibrium with soluble Aβ in the brain and blood (Kawarabayashi T, et al., *J. Neurosci.* (2001) 21:372–381).

As described in PCT application US00/35681 and U.S. Ser. No. 09/753,130 (now U.S. Pat. No. 6,465,195, issued Oct. 15, 2000) both incorporated herein by reference, total circulating levels of Aβ peptide in OSE are similar in normal individuals and individuals predisposed to exhibit the symptoms of Alzheimer's. However, $A\beta_{42}$ levels are lower on average in individuals with Alzheimer's disease (Nitsch, R. M., et al., *Ann. Neurol.* (1995) 37:512–518). It is known that $A\beta_{42}$ is more prone to aggregate than is $A\beta_{40}$, and when this happens, adverse consequences such as Aβ deposition in amyloid plaques, conversion of Aβ to toxic soluble forms, nerve cell damage, and behavioral impairment such as dementias ensue (Golde, T. E., et al., *Biochem. Biophys. Acta.* (2000) 1502:172–187).

Methods to induce an immune response to reduce amyloid deposits are described in PCT publication WO99/27944 published Jun. 10, 1999. The description postulates that full-length aggregated Aβ peptide would be a useful immunogen. Administration of a Aβ fragment (amino acids 13–28) conjugated to sheep anti-mouse IgG caused no change in cortex amyloid burden, and only one in nine animals that received injections of the Aβ 13–28 fragment-conjugate showed any lymphoproliferation in response to $A\beta_{40}$. The application also indicates that antibodies that specifically bind to Aβ peptide could be used as therapeutic agents. However, this appears to be speculation since the supporting data reflect protocols that involve active immunization using, for example, $A\beta_{42}$. The peptides are supplied using adjuvants and antibody titers formed from the immunization, as well as levels of Aβ peptide and of the precursor peptide, are determined. The publication strongly suggests that Aβ plaque must be reduced in order to alleviate Alzheimer's symptoms, and that cell-mediated processes are required for successful reduction of Aβ plaque.

WO 99/60024, published 25 Nov. 1999, is directed to methods for amyloid removal using anti-amyloid antibodies. The mechanism, however, is stated to utilize the ability of anti-Aβ antibodies to bind to pre-formed amyloid deposits (i.e., plaques) and result in subsequent local microglial clearance of localized plaques. This mechanism was not proved in vivo. This publication further states that to be effective against Aβ plaques, anti-Aβ antibodies must gain access to the brain parenchyma and cross the blood brain barrier.

Several PCT applications that relate to attempts to control amyloid plaques were published on 7 Dec. 2000. WO 00/72880 describes significant reduction in plaque in cortex and hippocampus in a transgenic mouse model of Alzheimer's disease when treated using N-terminal fragments of Aβ peptides and antibodies that bind to them, but not when treated with the Aβ 13–28 fragment conjugated to sheep anti-mouse IgG or with an antibody against the 13–28 fragment, antibody 266. The N-terminal directed antibodies were asserted to cross the blood-brain barrier and to induce phagocytosis of amyloid plaques in in vitro studies.

WO 00/72876 has virtually the same disclosure as WO 00/72880 and is directed to immunization with the amyloid fibril components themselves.

WO 00/77178 describes antibodies that were designed to catalyze the hydrolysis of β-amyloid, including antibodies raised against a mixture of the phenylalanine statine transition compounds Cys-$A\beta_{10-25}$, statine $Phe_{19}$-$Phe_{20}$ and Cys-$Ap_{10-25}$ statine $Phe_{20}$-$Ala_{21}$ and antibodies raised against $A\beta_{10-25}$ having a reduced amide bond between $Phe_{19}$ and $Phe_{20}$. This document mentions sequestering of Aβ, but this is speculation because it gives no evidence of such sequestering. Further, the document provides no in vivo evidence that administration of antibodies causes efflux of Aβ from the central nervous system, interferes with plaque formation, reduces plaque burden, forms complexes between the antibodies and Aβ in tissue samples, or affects cognition.

It has been shown that one pathway for Aβ metabolism is via transport from CNS to the plasma (Zlokovic, B. V., et al., *Proc. Natl. Acad. Sci (USA)* (1996) 93:4229–4234; Ghersi-Egea, J-F., et al., *J. Neurochem.* (1996) 67:880–883). Additionally, it has been shown that Aβ in plasma can cross the blood-brain-barrier and enter the brain (Zlokovic, B. V., et al., *Biochem. Biophys. Res. Comm.* (1993) 67:1034–1040). It has also been shown that administration of certain polyclonal and monoclonal Aβ antibodies decreases Aβ deposition in amyloid plaques in the APP$^{V717F}$ transgenic mouse model of Alzheimer's disease (Bard, F., et al., *Nature Med.* (2000) 6:916–919); however, this was said to be due to certain anti-Aβ antibodies crossing the blood-brain-barrier stimulating phagocytose of amyloid plaques by microglial cells. In Bard's experiments, assays of brain slices ex vivo showed that the presence of added Aβ antibody, along with exogenously added microglia, induced phagocytosis of Aβ, resulting in removal of Aβ deposits.

The levels of both soluble Aβ$_{40}$ and Aβ$_{42}$ in CSF and blood can readily be detected using standardized assays using antibodies directed against epitopes along the Aβ chain. Such assays have been reported, for example, in U.S. Pat. Nos. 5,766,846; 5,837,672; and 5,593,846. These patents describe the production of murine monoclonal antibodies to the central domain of the Aβ peptide, and these were reported to have epitopes around and including positions 16 and 17. Antibodies directed against the N-terminal region were described as well. Several monoclonal antibodies were asserted to immunoreact with positions 13–28 of the Aβ peptide; these did not bind to a peptide representing positions 17–28, thus, according to the cited patents, establishing that it is this region, including positions 16–17 (the α-secretase site) that was the target of these antibodies. Among antibodies known to bind between amino acids 13 and 28 of Aβ are mouse antibodies 266, 4G8, and 1C2.

We have now unexpectedly found that administration of the 266 antibody very quickly and almost completely restores cognition (object memory) in 24-month old hemizygous transgenic mice (APP$^{V717F}$). Yet, the antibody does not have the properties that the art teaches are required for an antibody to be effective in treating Alzheimer's disease, Down's syndrome, and other conditions related to the Aβ peptide. To our further surprise, we observed that antibodies that bind Aβ between positions 13 and 28 (266 and 4G8) are capable of sequestering soluble forms of Aβ from their bound, circulating forms in the blood, and that peripheral administration of antibody 266 results in rapid efflux of relatively large quantities of Aβ peptide from the CNS into the plasma. This results in altered clearance of soluble Aβ, prevention of plaque formation, and, most surprisingly, improvement in cognition, even without necessarily reducing Aβ amyloid plaque burden, crossing the blood brain barrier to any significant extent, decorating plaque, activating cellular mechanisms, or binding with great affinity to aggregated Aβ.

DISCLOSURE OF THE INVENTION

The invention provides humanized antibodies, or fragments thereof, that positively affect cognition in diseases and conditions where Aβ may be involved, such as clinical or pre-clinical Alzheimer's disease, Down's syndrome, and clinical or pre-clinical cerebral amyloid angiopathy. The antibodies or fragments thereof need not cross the blood-brain barrier, decorate amyloid plaque, activate cellular responses, or even necessarily reduce amyloid plaque burden. In another aspect, this invention provides humanized antibodies and fragments thereof that sequester Aβ peptide from its bound, circulating form in blood, and alter clearance of soluble and bound forms of Aβ in central nervous system and plasma. In another aspect, this invention provides humanized antibodies and fragments thereof, wherein the humanized antibodies specifically bind to an epitope between amino acids 13 and 28 of the Aβ molecule. In another aspect, the invention provides humanized antibodies and fragments thereof, wherein the CDR are derived from mouse monoclonal antibody 266 and wherein the antibodies retain approximately the binding properties of the mouse antibody and have in vitro and in vivo properties functionally equivalent to the mouse antibody (sequences SEQ ID NO:1 through SEQ ID NO:6). In another aspect, this invention provides humanized antibodies and fragments thereof, wherein the variable regions have sequences comprising the CDR from mouse antibody 266 and specific human framework sequences (sequences SEQ ID NO:7-SEQ ID NO:10), wherein the antibodies retain approximately the binding properties of the mouse antibody and have in vitro and in vivo properties functionally equivalent to the mouse antibody 266. In another aspect, this invention provides humanized antibodies and fragments thereof, wherein the light chain is SEQ ID NO:11 and the heavy chain is SEQ ID NO:12.

Also part of the invention are polynucleotide sequences that encode the humanized antibodies or fragments thereof disclosed above, vectors comprising the polynucleotide sequences encoding the humanized antibodies or fragments thereof, host cells transformed with the vectors or incorporating the polynucleotides that express the humanized antibodies or fragments thereof, pharmaceutical formulations of the humanized antibodies and fragments thereof disclosed herein, and methods of making and using the same.

Such humanized antibodies and fragments thereof are useful for sequestering Aβ in humans; for treating and preventing diseases and conditions characterized by Aβ plaques or Aβ toxicity in the brain, such as Alzheimer's disease, Down's syndrome, and cerebral amyloid angiopathy in humans; for diagnosing these diseases in humans; and for determining whether a human subject will respond to treatment using human antibodies against Aβ.

Administration of an appropriate humanized antibody in vivo to sequester Aβ peptide circulating in biological fluids is useful for preventive and therapeutic treatment of conditions associated with the formation of Aβ-containing diffuse, neuritic, and cerebrovascular plaques in the brain. The humanized antibody, including an immunologically reactive fragment thereof, results in removal of the Aβ peptide from macromolecular complexes which would normally be relevant in transporting it in body fluids to and from sites where plaques can form or where it can be toxic. In addition, sequestering of plasma Aβ peptide with the antibody or fragment thereof behaves as a "sink," effectively sequestering soluble Aβ peptide in the plasma compartment, and inducing Aβ to enter the plasma from locations in the central nervous system (CNS). By sequestering Aβ in the blood, net efflux from the brain is enhanced and soluble Aβ is prevented from depositing in insoluble plaques and from forming toxic soluble species in the brain. In addition, insoluble Aβ in plaques which is in equilibrium with soluble Aβ can be removed from the brain through a sequestering effect in the blood. Sequestering the Aβ peptide with the antibody also enhances its removal from the body and inhibits toxic effects of soluble Aβ in the brain and the development and further accumulation of insoluble Aβ as amyloid in plaques. The antibodies useful in the invention do not cross the blood-brain barrier in large amounts ($\leq 0.1\%$ plasma levels). In addition, humanized antibodies used in the invention, when administered peripherally, do not need to elicit a cellular immune response in brain when bound to Aβ peptide or when freely circulating to have their beneficial effects. Further, when administered peripherally they do not need to appreciably bind aggregated Aβ peptide in the brain to have their beneficial effects.

Thus, in one aspect, the invention is directed to a method to treat and to prevent conditions characterized by the formation of plaques containing beta-amyloid protein in humans, which method comprises administering, preferably peripherally, to a human in need of such treatment a therapeutically or prophylactically effective amount of humanized monoclonal antibody or immunologically reactive fragment thereof, which antibody specifically binds to the mid-region of the Aβ peptide. In another aspect, the invention is directed to a method to inhibit the formation of amyloid plaques and to clear amyloid plaques in humans, which method comprises administering to a human subject in need of such inhibition an effective amount of a humanized antibody that sequesters Aβ peptide from its circulating form in blood and induces efflux out of the brain as well as altered Aβ clearance in plasma and the brain. In additional aspects, the invention is directed to such humanized antibodies, including immunologically effective portions thereof, and to methods for their preparation.

The invention also includes methods of reversing cognitive decline, improving cognition, treating cognitive decline, and preventing cognitive decline in a subject diagnosed with clinical or pre-clinical Alzheimer's disease, Down's syndrome, or clinical or pre-clinical cerebral amyloid angiopathy, comprising administering to the subject an effective amount of a humanized antibody of the invention.

The invention also includes use of a humanized antibody of the invention for the manufacture of a medicament, including prolonged expression of recombinant sequences of the antibody or antibody fragment in human tissues, for treating, preventing, or reversing Alzheimer's disease, Down's syndrome, or cerebral amyloid angiopathy; for treating, preventing, or reversing cognitive decline in clinical or pre-clinical Alzheimer's disease, Down's syndrome, or clinical or pre-clinical cerebral amyloid angiopathy; or to inhibit the formation of amyloid plaques or the effects of toxic soluble Aβ species in humans.

The invention is related to the surprising observation that within a short period of time after administration of an antibody of the present invention, relatively large quantities of Aβ efflux from the central nervous system to the blood. Thus, this invention includes methods to assess the response of a human subject to treatment with an antibody that binds Aβ or a fragment thereof, comprising: a) administering the antibody or a fragment thereof to the subject; and b) measuring the concentration of Aβ in the subject's blood.

The invention also includes a method of treating a human subject with an antibody that binds Aβ or a fragment thereof, comprising: a) administering a first amount of the antibody or fragment thereof to the subject; b) within 3 hours to two weeks after administering the first dose, measuring the concentration of Aβ in the subject's blood; c) if necessary, calculating a second amount of antibody or fragment thereof based on the result of step b), which second amount is the same as or different than the first amount; and d) administering the second amount of antibody or fragment.

The invention also includes a method of assessing in a human subject the efficacy of an antibody that binds to Aβ, or a fragment thereof, for inhibiting or preventing Aβ amyloid plaque formation, for reducing Aβ amyloid plaque, for reducing the effects of toxic soluble Aβ species, or for treating a condition or a disease associated with Aβ plaque, comprising: a) obtaining a first sample of the subject's plasma or CSF; b) measuring a baseline concentration of Aβ in the first sample; c) administering the antibody or fragment thereof to the subject; d) within 3 hours to two weeks after administering the antibody or fragment thereof, obtaining a second sample of the subject's plasma or CSF; and e) measuring the concentration of Aβ in the second sample; wherein, efficacy is related to the quantity of Aβ bound to the antibody in the blood and the concentration of Aβ in the CSF.

BRIEF DESCRIPTION OF THE DRAWINGS

FIG. 4 shows the polynucleotide sequences for expressing 266 light chain from plasmid pVk-Hu266 and the single amino acid codes for the expressed humanized 266 light chain (corresponding to SEQ ID NO:11 when mature). The complete sequence of the Hu266 light chain gene is located between the MluI and BamHI sites in pVk-Hu266. The nucleotide number indicates its position in pVgk-Hu266. The $V_k$ and $C_k$ exons are translated in single letter code; the dot indicates the translation termination codon. The mature heavy chain starts at the double-underlined aspartic acid (D). The intron sequences are in italic.

FIG. 5 shows the polynucleotide sequences for expressing 266 heavy chain from plasmid pVg1-Hu266 and the single amino acid codes for the expressed humanized 266 heavy chain (corresponding to SEQ ID NO:12 when mature). The complete sequence of the Hu266 heavy chain gene is located between the MluI and BamHI sites in pVg1-Hu266. The nucleotide number indicates its position in pVg1-Hu266. The $V_h$ and $C_h$ exons are translated in single letter code; the dot indicates the translation termination codon. The mature heavy chain starts at the double-underlined glutamic acid (E). The intron sequences are in italic.

MODES OF CARRYING OUT THE INVENTION

Figure 1:
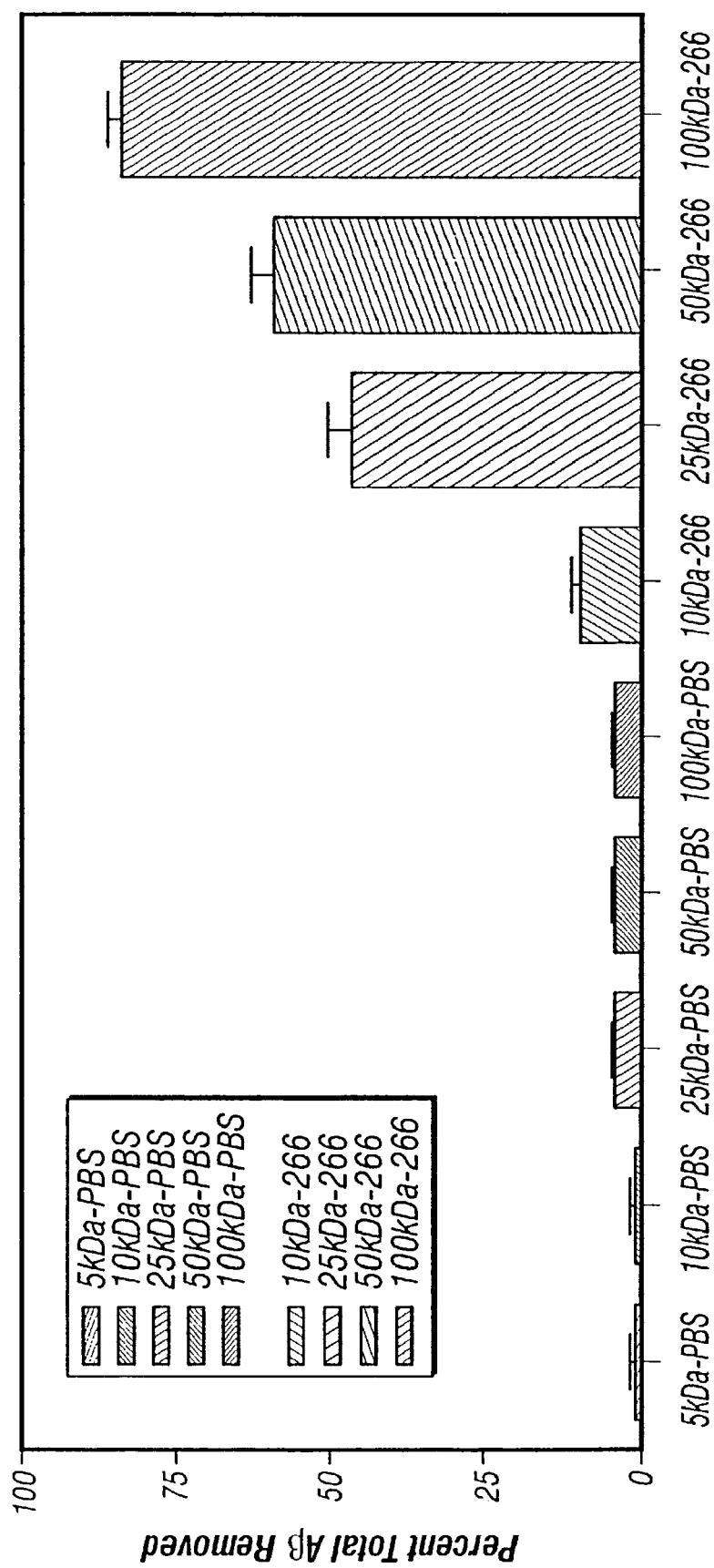
FIG. 1 shows the percentage of the Aβ peptide withdrawn from human cerebrospinal fluid through a dialysis membrane by Mab 266 as a function of the molecular weight cutoff of the dialysis membrane.

The Aβ peptides that circulate in human biological fluids represent the carboxy terminal region of a precursor protein encoded on chromosome 21. It has been reported from the results of in vitro experiments that the Aβ peptide has poor solubility in physiological solutions, since it contains a stretch of hydrophobic amino acids which are a part of the region that anchors its longer precursor to the lipid membranes of cells. It is thus not surprising that circulating Aβ peptide is normally complexed with other moieties that prevent it from aggregating. This has resulted in difficulties in detecting circulating Aβ peptide in biological fluids.

The above-mentioned patent documents (U.S. Pat. Nos. 5,766,846; 5,837,672 and 5,593,846) describe the preparation of antibodies, including a monoclonal antibody, designated clone 266 which was raised against, and has been shown to bind specifically to, a peptide comprising amino acids 13–28 of the Aβ peptide. The present applicants have found that antibodies that bind within this region, in contrast to antibodies that bind elsewhere in the amino acid sequence of Aβ, are able to sequester the soluble Aβ peptide very effectively from macromolecular complexes. This sequestration will effect net Aβ peptide efflux from the CNS, alter its clearance in CNS and plasma, and reduce its availability for plaque formation. Thus, antibodies of this specificity, modified to reduce their immunogenicity by converting them to a humanized form, offer the opportunity to treat, both prophylactically and therapeutically, conditions that are associated with formation of beta-amyloid plaques. These conditions include, as noted above, pre-clinical and clinical Alzheimer's, Down's syndrome, and pre-clinical and clinical cerebral amyloid angiopathy.

As used herein, the word "treat" includes therapeutic treatment, where a condition to be treated is already known to be present and prophylaxis—i.e., prevention of, or amelioration of, the possible future onset of a condition.

By "monoclonal antibodies that bind to the mid-region of Aβ peptide" is meant monoclonal antibodies (Mab or Mabs) that bind an amino acid sequence representing an epitope contained between positions 13–28 of Aβ. The entire region need not be targeted. As long as the antibody binds at least an epitope within this region (especially, e.g., including the α-secretase site 16–17 or the site at which antibody 266 binds), such antibodies are effective in the method of the invention.

By "antibody" is meant a monoclonal antibody per se, or an immunologically effective fragment thereof, such as an $F_{ab}$, $F_{ab'}$, or $F_{(ab')2}$ fragment thereof. In some contexts, herein, fragments will be mentioned specifically for emphasis; nevertheless, it will be understood that regardless of whether fragments are specified, the term "antibody" Includes such fragments as well as single-chain forms. As long as the protein retains the ability specifically to bind its intended target, and in this case, to sequester Aβ peptide from its carrier proteins in blood, it is included within the term "antibody." Also included within the definition "antibody" for example, are single chain forms, generally designated $F_v$ regions, of antibodies with this specificity. Preferably, but not necessarily, the antibodies useful in the invention are produced recombinantly, as manipulation of the typically murine or other non-human antibodies with the appropriate specificity is required in order to convert them to humanized form. Antibodies may or may not be glycosylated, though glycosylated antibodies are preferred. Antibodies are properly cross-linked via disulfide bonds, as is well-known.

The basic antibody structural unit is known to comprise a tetramer. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as gamma, mu, alpha, and lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids.

The variable regions of each light/heavy chain pair form the antibody binding site. Thus, an intact antibody has two binding sites. The chains all exhibit the same general structure of relatively conserved framework regions (FR) joined by three hypervariable regions, also called complementarily determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with well known conventions [Kabat "Sequences of Proteins of Immunological Interest" National Institutes of Health, Bethesda, Md., 1987 and 1991; Chothia, et al., J. Mol. Biol. 196:901–917 (1987); Chothia, et al., Nature 342:878–883 (1989)].

As is well understood in the art, monoclonal antibodies can readily be generated with appropriate specificity by standard techniques of immunization of mammals, forming hybridomas from the antibody-producing cells of said mammals or otherwise immortalizing them, and culturing the hybridomas or immortalized cells to assess them for the appropriate specificity. In the present case such antibodies could be generated by immunizing a human, rabbit, rat or mouse, for example, with a peptide representing an epitope encompassing the 13–28 region of the Aβ peptide or an appropriate subregion thereof. Materials for recombinant manipulation can be obtained by retrieving the nucleotide sequences encoding the desired antibody from the hybridoma or other cell that produces it. These nucleotide sequences can then be manipulated to provide them in humanized form.

By "humanized antibody" is meant an antibody that is composed partially or fully of amino acid sequences derived from a human antibody germline by altering the sequence of an antibody having non-human complementarity determining regions (CDR). The simplest such alteration may consist simply of substituting the constant region of a human antibody for the murine constant region, thus resulting in a human/murine chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. Fully human antibodies are produced in genetically modified mice whose immune systems have been altered to correspond to human immune systems. As mentioned above, it is sufficient for use in the methods of the invention, to employ an immunologically specific fragment of the antibody, including fragments representing single chain forms.

A humanized antibody again refers to an antibody comprising a human framework, at least one CDR from a non-human antibody, and in which any constant region present is substantially identical to a human immunoglobulin constant region, i.e., at least about 85–90%, preferably at least 95% identical. Hence, all parts of a humanized antibody, except possibly the CDRs, are substantially identical to corresponding parts of one or more native human immunoglobulin sequences. For example, a humanized immunoglobulin would typically not encompass a chimeric mouse variable region/human constant region antibody.

Humanized antibodies have at least three potential advantages over non-human and chimeric antibodies for use in human therapy:

1) because the effector portion is human, it may interact better with the other parts of the human immune system (e.g., destroy the target cells more efficiently by complement-dependent cytotoxicity (CDC) or antibody-dependent cellular cytotoxicity (ADCC)).

2) The human immune system should not recognize the framework or C region of the humanized antibody as foreign, and therefore the antibody response against such an injected antibody should be less than against a totally foreign non-human antibody or a partially foreign chimeric antibody.

3) Injected non-human antibodies have been reported to have a half-life in the human circulation much shorter than the half-life of human antibodies. Injected humanized antibodies will have a half-life essentially identical to naturally occurring human antibodies, allowing smaller and less frequent doses to be given.

The design of humanized immunoglobulins may be carried out as follows. When an amino acid falls under the following category, the framework amino acid of a human immunoglobulin to be used (acceptor immunoglobulin) is replaced by a framework amino acid from a CDR-providing non-human immunoglobulin (donor immunoglobulin):

(a) the amino acid in the human framework region of the acceptor immunoglobulin is unusual for human immunoglobulin at that position, whereas the corresponding amino acid in the donor immunoglobulin is typical for human immunoglobulin at that position;

(b) the position of the amino acid is immediately adjacent to one of the CDRs; or (c) any side chain atom of a framework amino acid is within about 5–6 angstroms (center-to-center) of any atom of a CDR amino acid in a three dimensional immunoglobulin model [Queen, et al., op. cit., and Co, et al., *Proc. Natl. Acad. Sci. USA* 88, 2869 (1991)]. When each of the amino acid in the human framework region of the acceptor immunoglobulin and a corresponding amino acid in the donor immunoglobulin is unusual for human immunoglobulin at that position, such an amino acid is replaced by an amino acid typical for human immunoglobulin at that position.

A preferred humanized antibody is a humanized form of mouse antibody 266. The CDRs of humanized 266 have the following amino acid sequences:

```
light chain CDR1:
1                   5                           10                      15
Arg Ser Ser Gln Ser Leu Ile Tyr Ser Asp Gly Asn Ala Tyr Leu His     (SEQ ID NO:1)

light chain CDR2:
1               5
Lys Val Ser Asn Arg Phe Ser                                         (SEQ ID NO:2)

light chain CDR3:
1                   5
Ser Gln Ser Thr His Val Pro Trp Thr                                 (SEQ ID NO:3)

heavy chain CDR1:
1               5
Arg Tyr Ser Met Ser                                                 (SEQ ID NO:4)

heavy chain CDR2:
1                   5                           10                      15
Gln Ile Asn Ser Val Gly Asn Ser Thr Tyr Tyr Pro Asp Thr Val Lys Gly (SEQ ID NO:5)

and, heavy chain CDR3:
1
Gly Asp Tyr.                                                        (SEQ ID NO:6)
```

A preferred light chain variable region of a humanized antibody of the present invention has the following amino acid sequence, in which the framework originated from human germline Vk segments DPK18 and J segment Jk1, with several amino acid substitutions to the consensus amino acids in the same human V subgroup to reduce potential immunogenicity:

```
1                   5                           10                      15
Asp Xaa Val Met Thr Gln Xaa Pro Leu Ser Leu Pro Val Xaa Xaa (SEQ ID NO:7)

20                          25                      30
Gly Gln Pro Ala Ser Ile Ser Cys Arg Ser Ser Gln Ser Leu Xaa 35                          40                      45
Tyr Ser Asp Gly Asn Ala Tyr Leu His Trp Phe Leu Gln Lys Pro 50                          55                      60
Gly Gln Ser Pro Xaa Leu Leu Ile Tyr Lys Val Ser Asn Arg Phe 65                          70                      75
Ser Gly Val Pro Asp Ary Phe Ser Gly Ser Gly Ser Gly Thr Asp 80                          85                      90
Phe Thr Leu Lys Ile Ser Arg Val Glu Ala Glu Asp Xaa Gly Val 95                          100                     105
Tyr Tyr Cys Ser Gln Ser Thr His Val Pro Trp Thr Phe Gly Xaa

110
Gly Thr Xaa Xaa Glu Ile Lys Arg
``` wherein:
Xaa at position 2 is Val or Ile;
Xaa at position 7 is Ser or Thr;
Xaa at position 14 is Thr or Ser;
Xaa at position 15 is Leu or Pro;
Xaa at position 30 is Ile or Val;
Xaa at position 50 is Arg, Gln, or Lys;
Xaa at position 88 is Val or Leu;
Xaa at position 105 is Gln or Gly;
Xaa at position 108 is Lys or Arg; and
Xaa at position 109 is Val or Leu.

A preferred heavy chain variable region of a humanized antibody of the present invention has the following amino acid sequence, in which the framework originated from human germline VH segments DP53 and J segment JH4, with several amino acid substitutions to the consensus amino acids in the same human subgroup to reduce potential immunogenicity:

```
            1                   5                      10                     15
          Xaa Val Gln Leu Val Glu Xaa Gly Gly Gly Leu Val Gln Pro Gly  (SEQ ID NO:8)

20                      25                     30
          Gly Ser Leu Arg Leu Ser Cys Ala Ala Ser Gly Phe Thr Phe Ser 35                      40                     45
          Arg Tyr Ser Met Ser Trp Val Arg Gln Ala Pro Gly Lys Gly Leu 50                      55                     60
          Xaa Leu Val Ala Gln Ile Asn Ser Val Gly Asn Ser Thr Tyr Tyr 65                      70                     75
          Pro Asp Xaa Val Lys Gly Arg Phe Thr Ile Ser Arg Asp Asn Xaa 80                      85                     90
          Xaa Asn Thr Leu Tyr Leu Gln Met Asn Ser Leu Arg Ala Xaa Asp 95                     100                    105
          Thr Ala Val Tyr Tyr Cys Ala Ser Gly Asp Tyr Trp Gly Gln Gly

110
          Thr Xaa Val Thr Val Ser Ser
``` wherein:

Xaa at position 1 is Glu or Gln;
Xaa at position 7 is Ser or Leu;
Xaa at position 63 is Thr or Ser;
Xaa at position 75 is Ala, Ser, Val, or Thr;
Xaa at position 76 is Lys or Arg;
Xaa at position 89 is Glu or Asp; and
Xaa at position 107 is Leu or Thr.

A particularly preferred light chain variable region of a humanized antibody of the present invention has the following amino acid sequence, in which the framework originated from human germline Vk segments DPK18 and J segment Jk1, with several amino acid substitutions to the consensus amino acids in the same human V subgroup to reduce potential immunogenicity:

```
            1                   5                      10                     15
          Asp Val Val Met Thr Gln Ser Pro Leu Ser Leu Pro Val Thr Leu  (SEQ ID NO:9)

20                      25                     30
          Gly Gln Pro Ala Ser Ile Ser Cys Arg Ser Ser Gln Ser Leu Ile 35                      40                     45
          Tyr Ser Asp Gly Asn Ala Tyr Leu His Trp Phe Leu Gln Lys Pro 50                      55                     60
          Gly Gln Ser Pro Arg Leu Leu Ile Tyr Lys Val Ser Asn Arg Phe 65                      70                     75
          Ser Gly Val Pro Asp Arg Phe Ser Gly Ser Gly Ser Gly Thr Asp 80                      85                     90
          Phe Thr Leu Lys Ile Ser Arg Val Glu Ala Gln Asp Val Gly Val 95                     100                    105
          Tyr Tyr Cys Ser Gln Ser Thr His Val Pro Trp Thr Phe Gly Gln

110
          Gly Thr Lys Val Gln Ile Lys Arg.
```

Xaa at position 46 is Glu, Val, Asp, or Ser;

A particularly preferred heavy chain variable region of a humanized antibody of the present invention has the following amino acid sequence, in which the framework originated from human germline VH segments DP53 and J segment JH4:

```
          1               5              10              15
         Glu Val Gln Leu Val Glu Ser Gly Gly Leu Val Gln Pro Gly  (SEQ ID NO:10)
                         20              25              30
         Gly Ser Leu Arg Leu Ser Cys Ala Ala Ser Gly Phe Thr Phe Ser
                         35              40              45
         Arg Tyr Ser Met Ser Trp Val Arg Gln Ala Pro Gly Lys Gly Leu
                         50              55              60
         Glu Leu Val Ala Gln Ile Asn Ser Val Gly Asn Ser Thr Tyr Tyr
                         65              70              75
         Pro Asp Thr Val Lys Gly Ary Phe Thr Ile Ser Arg Asp Asn Ala
                         80              85              90
         Lys Asn Thr Leu Tyr Leu Gln Met Asn Ser Leu Arg Ala Glu Asp
                         95             100             105
         Thr Ala Val Tyr Tyr Cys Ala Ser Gly Asp Tyr Trp Gly Gln Gly
                        110
         Thr Leu Val Thr Val Ser Ser.
```

A preferred light chain for a humanized antibody of the present invention has the amino acid sequence:

```
          1               5              10              15
         Asp Val Val Met Thr Gln Ser Pro Leu Ser Leu Pro Val Thr Leu  (SEQ ID NO:11)
                         20              25              30
         Gly Gln Pro Ala Ser Ile Ser Cys Arg Ser Ser Gln Ser Leu Ile
                         35              40              45
         Tyr Ser Asp Gly Asn Ala Tyr Leu His Trp Phe Leu Gln Lys Pro
                         50              55              60
         Gly Gln Ser Pro Arg Leu Leu Ile Tyr Lys Val Ser Asn Arg Phe
                         65              70              75
         Ser Gly Val Pro Asp Arg Phe Ser Gly Ser Gly Ser Gly Thr Asp
                         80              85              90
         Phe Thr Leu Lys Ile Ser Arg Val Glu Ala Glu Asp Val Gly Val
                         95             100             105
         Tyr Tyr Cys Ser Gln Ser Thr His Val Pro Trp Thr Phe Gly Gln
                        110             115             120
         Gly Thr Lys Val Glu Ile Lys Arg Thr Val Ala Ala Pro Ser Val
                        125             130             135
         Phe Ile Phe Pro Pro Ser Asp Glu Gln Leu Lys Ser Gly Thr Ala
                        140             145             150
         Ser Val Val Cys Leu Leu Asn Asn Phe Tyr Pro Arg Glu Ala Lys
                        155             160             165
         Val Gln Trp Lys Val Asp Asn Ala Leu Gln Ser Gly Asn Ser Gln
                        170             175             180
         Glu Ser Val Thr Glu Gln Asp Ser Lys Asp Ser Thr Tyr Ser Leu
                        185             190             195
         Ser Ser Thr Leu Thr Leu Ser Lys Ala Asp Tyr Glu Lys His Lys
                        200             205             210
         Val Tyr Ala Cys Glu Val Thr His Gln Gly Leu Ser Ser Pro Val
                        215
         Thr Lys Ser Phe Asn Arg Gly Glu Cys.
```

A preferred heavy chain for a humanized antibody of the present invention has the amino acid sequence:

```
  1               5                  10                  15
Glu Val Gln Leu Val Glu Ser Gly Gly Gly Leu Val Gln Pro Gly  (SEQ ID NO:12)

20                  25                  30
Gly Ser Leu Arg Leu Ser Cys Ala Ala Ser Gly Phe Thr Phe Ser 35                  40                  45
Arg Tyr Ser Met Ser Trp Val Ary Gln Ala Pro Gly Lys Gly Leu 50                  55                  60
Glu Leu Val Ala Gln Ile Asn Ser Val Gly Asn Ser Thr Tyr Tyr 65                  70                  75
Pro Asp Thr Val Lys Gly Arg Phe Thr Ile Ser Arg Asp Asn Ala 80                  85                  90
Lys Asn Thr Leu Tyr Leu Gln Met Asn Ser Leu Arg Ala Glu Asp 95                 100                 105
Thr Ala Val Tyr Tyr Cys Ala Ser Gly Asp Tyr Trp Gly Gln Gly 110                 115                 120
Thr Leu Val Thr Val Ser Ser Ala Ser Thr Lys Gly Pro Ser Val 125                 130                 135
Phe Pro Leu Ala Pro Ser Ser Lys Ser Thr Ser Gly Gly Thr Ala 140                 145                 150
Ala Leu Gly Cys Leu Val Lys Asp Tyr Phe Pro Glu Pro Val Thr 155                 160                 165
Val Ser Trp Asn Ser Gly Ala Leu Thr Ser Gly Val His Thr Phe 170                 175                 180
Pro Ala Val Leu Gln Ser Ser Gly Leu Tyr Ser Leu Ser Ser Val 185                 190                 195
Val Thr Val Pro Ser Ser Ser Leu Gly Thr Gln Thr Tyr Ile Cys 200                 205                 210
Asn Val Asn His Lys Pro Ser Asn Thr Lys Val Asp Lys Lys Val 215                 220                 225
Glu Pro Lys Ser Cys Asp Lys Thr His Thr Cys Pro Pro Cys Pro 230                 235                 240
Ala Pro Glu Leu Leu Gly Gly Pro Ser Val Phe Leu Phe Pro Pro 245                 250                 255
Lys Pro Lys Asp Thr Leu Met Ile Ser Arg Thr Pro Glu Val Thr 260                 265                 270
Cys Val Val Val Asp Val Ser His Glu Asp Pro Glu Val Lys Phe 275                 280                 285
Asn Trp Tyr Val Asp Gly Val Glu Val His Asn Ala Lys Thr Lys 290                 295                 300
Pro Arg Glu Glu Gln Tyr Asn Ser Thr Tyr Arg Val Val Ser Val 305                 310                 315
Leu Thr Val Leu His Gln Asp Trp Leu Asn Gly Lys Glu Tyr Lys 320                 325                 330
Cys Lys Val Ser Asn Lys Ala Leu Pro Ala Pro Ile Glu Lys Thr 335                 340                 345
Ile Ser Lys Ala Lys Gly Gln Pro Ary Glu Pro Gln Val Tyr Thr 350                 355                 360
Leu Pro Pro Ser Arg Asp Glu Leu Thr Lys Asn Gln Val Ser Leu 365                 370                 375
Thr Cys Leu Val Lys Gly Phe Tyr Pro Ser Asp Ile Ala Val Glu 380                 385                 390
```

```
                            -continued
Trp Glu Ser Asn Gly Gln Pro Glu Aso Asn Tyr Lys Thr Thr Pro 395                 400                 405
Pro Val Leu Asp Ser Asp Gly Ser Phe Phe Leu Tyr Ser Lys Leu 410                 415                 420
Thr Val Asp Lys Ser Arg Trp Gln Gln Gly Asn Val Phe Ser Cys 425                 430                 435
Ser Val Met His Glu Ala Leu His Asn His Tyr Thr Gln Lys Ser 440
Leu Ser Leu Ser Pro Gly Lys.
```

Other sequences are possible for the light and heavy chains for the humanized antibodies of the present invention and for humanized 266. The immunoglobulins can have two pairs of light chain/heavy chain complexes, at least one chain comprising one or more mouse complementarity determining regions functionally joined to human framework region segments.

In another aspect, the present invention is directed to recombinant polynucleotides encoding antibodies which, when expressed, comprise the heavy and light chain CDRs from an antibody of the present invention. As to the human framework region, a framework or variable region amino acid sequence of a CDR-providing non-human immunoglobulin is compared with corresponding sequences in a human immunoglobulin variable region sequence collection, and a sequence having a high percentage of identical amino acids is selected. Exemplary polynucleotides, which on expression code for the polypeptide chains comprising the heavy and light chain CDRs of monoclonal antibody 266 are given in FIGS. 4 and 5. Due to codon degeneracy and non-critical amino-acid substitutions, other polynucleotide sequences can be readily substituted for those sequences. Particularly preferred polynucleotides of the present invention encode antibodies, which when expressed, comprise the CDRs of SEQ ID NO:1–SEQ ID NO:6, or any of the variable regions of SEQ ID NO:7–SEQ ID NO:10, or the light and heavy chains of SEQ ID NO:11 and SEQ ID NO:12.

The polynucleotides will typically further include an expression control polynucleotide sequence operably linked to the humanized immunoglobulin encoding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host cell line, the host cell is propagated under conditions suitable for high level expression of the nucleotide sequences, and, as desired, the collection and purification of the light chains, heavy chains, light/heavy chain dimers or intact antibodies, binding fragments or other immunoglobulin forms may follow.

The nucleotide sequences of the present invention capable of ultimately expressing the desired humanized antibodies can be formed from a variety of different polynucleotides (genomic or cDNA, RNA, synthetic oligonucleotides, etc.) and components (e.g., V, J, D, and C regions), as well as by a variety of different techniques. Joining appropriate genomic and synthetic sequences is a common method of production, but cDNA sequences may also be utilized.

Human constant region DNA sequences can be isolated in accordance with well known procedures from a variety of human cells, but preferably from immortalized B-cells. The CDRs for producing the immunoglobulins of the present invention will be similarly derived from non-human monoclonal antibodies capable of binding to an epitope between amino acids 13 and 28 of the Aβ peptide, which monoclonal antibodies are produced in any convenient mammalian source, including, mice, rats, rabbits, or other vertebrates capable of producing antibodies by well known methods, as described above. Suitable source cells for the polynucleotide sequences and host cells for immunoglobulin expression and secretion can be obtained from a number of sources well-known in the art.

In addition to the humanized immunoglobulins specifically described herein, other "substantially homologous" modified immunoglobulins can be readily designed and manufactured utilizing various recombinant DNA techniques well known to those skilled in the art. For example, the framework regions can vary from the native sequences at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis.

Alternatively, polypeptide fragments comprising only a portion of the primary antibody structure may be produced, which fragments possess one or more immunoglobulin activities (e.g., complement fixation activity). These polypeptide fragments may be produced by proteolytic cleavage of intact antibodies by methods well known in the art, or by inserting stop codons at the desired locations in vectors using site-directed mutagenesis, such as after CH1 to produce Fab fragments or after the hinge region to produce F(ab')$_2$ fragments. Single chain antibodies may be produced by joining VL and VH with a DNA linker.

As stated previously, the encoding nucleotide sequences will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences.

E. coli is a prokaryotic host useful particularly for cloning the polynucleotides of the present invention. Other microbial hosts suitable for use include bacilli, such as Bacillus subtilus, and other enterobacteriaceae, such as Salmonella, Serratia, and various Pseudomonas species. In these prokaryotic hosts, one can also make expression vectors, which will typically contain expression control sequences compatible with the host cell (e.g., an origin of replication).

In addition, any of a number of well-known promoters may be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. *Saccharomyces* is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention. Eukaryotic cells are actually preferred, because a number of suitable host cell lines capable of secreting intact immunoglobulins have been developed in the art, and include the CHO cell lines, various COS cell lines, Syrian Hamster Ovary cell lines, HeLa cells, preferably myeloma cell lines, transformed B-cells, human embryonic kidney cell lines, or hybridomas. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, cytomegalovirus and the like.

The vectors containing the nucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Once expressed, the whole antibodies, their dimers, individual light and heavy chains, or other immunoglobulin forms of the present invention can be purified according to standard procedures of the art, including ammonium sulfate precipitation, ion exchange, affinity, reverse phase, hydrophobic interaction column chromatography, gel electrophoresis and the like. Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically or prophylactically, as directed herein.

The antibodies (including immunologically reactive fragments) are administered to a subject at risk for or exhibiting Aβ-related symptoms or pathology such as clinical or preclinical Alzheimer's disease, Down's syndrome, or clinical or pre-clinical amyloid angiopathy, using standard administration techniques, preferably peripherally (i.e. not by administration into the central nervous system) by intravenous, intraperitoneal, subcutaneous, pulmonary, transdermal, intramuscular, intranasal, buccal, sublingual, or suppository administration. Although the antibodies may be administered directly into the ventricular system, spinal fluid, or brain parenchyma, and techniques for addressing these locations are well known in the art, it is not necessary to utilize these more difficult procedures. The antibodies of the invention are effective when administered by the more simple techniques that rely on the peripheral circulation system. The advantages of the present invention include the ability of the antibody exert its beneficial effects even though not provided directly to the central nervous system itself. Indeed, it has been demonstrated herein that the amount of antibody which crosses the blood-brain barrier is <0.1% of plasma levels and that the antibodies of the invention exert their ability to sequester Aβ in the peripheral circulation as well as to alter CNS and plasma soluble Aβ clearance.

The pharmaceutical compositions for administration are designed to be appropriate for the selected mode of administration, and pharmaceutically acceptable excipients such as dispersing agents, buffers, surfactants, preservatives, solubilizing agents, isotonicity agents, stabilizing agents and the like are used as appropriate. *Remington's Pharmaceutical Sciences*, Mack Publishing Co., Easton Pa., latest edition, incorporated herein by reference, provides a compendium of formulation techniques as are generally known to practitioners. It may be particularly useful to alter the solubility characteristics of the antibodies of the invention, making them more lipophilic, for example, by encapsulating them in liposomes or by blocking polar groups.

Peripheral systemic delivery by intravenous or intraperitoneal or subcutaneous injection is preferred. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl-N,N,N-trimethylammoniumchloride (DOTMA) or various compounds such as cholesterol hemisuccinate, phosphatidyl glycerols and the like.

The concentration of the humanized antibody in formulations from as low as about 0.1% to as much as 15 or 20% by weight and will be selected primarily based on fluid volumes, viscosities, and so forth, in accordance with the particular mode of administration selected. Thus, a typical pharmaceutical composition for injection could be made up to contain 1 mL sterile buffered water of phosphate buffered saline and 1–100 mg of the humanized antibody of the present invention. The formulation could be sterile filtered after making the formulation, or otherwise made microbiologically acceptable. A typical composition for intravenous infusion could have a volume as much as 250 mL of fluid, such as sterile Ringer's solution, and 1–100 mg per mL, or more in antibody concentration. Therapeutic agents of the invention can be frozen or lyophilized for storage and reconstituted in a suitable sterile carrier prior to use. Lyophilization and reconstitution can lead to varying degrees of antibody activity loss (e.g. with conventional immune globulins, IgM antibodies tend to have greater activity loss than IgG antibodies). Dosages may have to be adjusted to compensate. The pH of the formulation will be selected to balance antibody stability (chemical and physical) and comfort to the patient when administered. Generally, pH between 4 and 8 is tolerated.

Although the foregoing methods appear the most convenient and most appropriate for administration of proteins such as humanized antibodies, by suitable adaptation, other techniques for administration, such as transdermal administration and oral administration may be employed provided proper formulation is designed.

In addition, it may be desirable to employ controlled release formulations using biodegradable films and matrices, or osmotic mini-pumps, or delivery systems based on dextran beads, alginate, or collagen.

In summary, formulations are available for administering the antibodies of the invention and are well-known in the art and may be chosen from a variety of options.

Typical dosage levels can be optimized using standard clinical techniques and will be dependent on the mode of administration and the condition of the patient.

The following examples are intended to illustrate but not to limit the invention.

The examples hereinbelow employ, among others, a murine monoclonal antibody designated "266" which was originally prepared by immunization with a peptide composed of residues 13–28 of human Aβ peptide. The antibody was confirmed to immunoreact with this peptide, but had previously been reported to not react with the peptide containing only residues 17–28 of human Aβ peptide, or at any other epitopes within the Aβ peptide. The preparation of this antibody is described in U.S. Pat. No. 5,766,846, incorporated herein by reference. As the examples here describe experiments conducted in murine systems, the use of murine monoclonal antibodies is satisfactory. However, in the treatment methods of the invention intended for human use, humanized forms of the antibodies with the immunospecificity corresponding to that of antibody 266 are preferred.

EXAMPLE 1

Sequestration of Added Aβ Peptide in Human Fluids

Samples of human cerebrospinal fluid (CSF) (50 µl) and human plasma (50 µl) were incubated for 1 hour at room temperature as follows:

1. alone;

2. along with 5 ng Aβ 40 peptide; or 3. 5 ng Aβ 40 peptide plus 1 mg monoclonal antibody 266 (described, for example, in U.S. Pat. No. 5,766,846 incorporated herein by reference).

The samples were then electrophoresed on a 4–25% non-denaturing gradient gel, i.e., non-denaturing gradient electrophoresis (NDGGE) and transferred to nitrocellulose. The blots were then stained with Ponceau S or, for Western blot, probed with biotin-labeled monoclonal antibody (3D6) which is directed against the first five amino acids of Aβ peptide, developed with streptavidin-horse radish peroxidase and detected by enhanced chemiluminescence (ECL). The hydrated diameters of the materials contained in bands on the blots were estimated using Pharmacia molecular weight markers. Thus, if the Aβ peptide is bound to other molecules, it would run at the size of the resulting complex.

Western blots of CSF either with or without 5 ng Aβ peptide shows no evidence of the Aβ peptide in response to detection mediated by antibody 3D6. Similar results are obtained for human plasma. This was true despite the fact that Aβ peptide could be detected by SDS-PAGE followed by Western blot using the same technique and on the same CSF samples. Presumably, the detection of Aβ peptide was prevented by interactions between this peptide and other factors in the fluids tested. However, when Mab 266 is added to the incubation, characteristic bands representing sequestered Aβ peptide complexed to the antibody are present both in plasma and in CSF. The major band is at approximately 11 nm hydrated diameter, corresponding to antibody monomer with an additional smaller band at 13 nm corresponding to antibody dimer.

EXAMPLE 2

Specificity of the Sequestering Antibody

Samples containing 50 µl of human CSF or 10 µl of $APP^{V717F}$ CSF were used. $APP^{V717F}$ are transgenic mice representing a mouse model of Alzheimer's disease in which the human amyloid precursor protein transgene with a familial Alzheimer's disease mutation is expressed and results in the production of human Aβ peptide in the central nervous system.

The samples were incubated with or without various Mabs (1 µg) for 1 hour at room temperature and then electrophoresed on a 4–25% NDGGE and blotted onto nitrocellulose as described in Example 1. The antibodies were as follows:

Mab 266 (binds to positions 13–28);
Mab 4G8 (binds to positions 17–24);
QCBpan (rabbit polyclonal for positions 1–40);
mouse IgG (non-specific);
Mab 3D6 (binds to positions 1–5);
Mab 21F12 (binds to positions 33–42):
Mab 6E10 (binds to positions 1–17); and
$QCB_{40,42}$ (rabbit polyclonals to $A\beta_{40}$ and $A\beta_{42}$).

Detection of the Aβ peptide antibody complex was as described in Example 1—biotin labeled 3D6 (to the Aβ peptide N-terminus) followed by streptavidin-HRP and ECL. Similar detection in human CSF incubated with Mab 266, in some instances substituted $QCB_{40,42}$, which binds to the carboxyl terminus of Aβ peptide, for 3D6.

The results showed that of the antibodies tested, only Mab 4G8 and Mab 266 permitted the detection of Aβ peptide.

The results showed that for human CSF, only Mab 266 and Mab 4G8 were able to sequester in detectable amounts of an antibody Aβ complex (again, without any antibody, no Aβ is detected). Mab 266 was also able to produce similar results to those obtained with human CSF with CSF from $APP^{V717F}$ transgenic mice. Aβ peptide could be sequestered in human CSF using Mab 266 regardless of whether 3D6 or $QCB_{40,42}$ antibody was used to develop the Western blot.

EXAMPLE 3

Demonstration of Aβ3 Peptide-266 Complex by Two-Dimensional Electrophoresis

A sample containing 50 ng $A\beta_{40}$ peptide was incubated with 2 µg Mab 266 at 37° C. for 3 hours. A corresponding incubation of Mab 266 alone was used as a control.

The samples were then subjected to 2-dimensional gel electrophoresis.

In the first dimension, the incubated samples were subjected to NDGGE as described in Example 1. The polyacrylamide gel was then cut into individual lanes perpendicular to the direction of the first dimensional flow and gel separation under denaturing/reducing conditions by SDS-PAGE (Tricine urea gel) was performed in the second dimension. The presence of the bands was detected either by Ponceau-S staining (any protein) or by specific development using 6E10 Mab (Senetek, Inc.) and biotinylated anti-mouse Aβ in the HRP-based detection system.

Ponceau-S staining of the nitrocellulose blots after transfer permitted visualization of the heavy and light chains of Mab 266 alone. It was confirmed that Aβ peptide was in a complex with Mab 266 as a band at 4 kD was observed that aligns with the size of full-length Mab 266 seen after the first dimension NDGGE.

EXAMPLE 4

Demonstration of Non-Equivalence of Binding and Sequestration

Aβ peptide as it circulates in plasma and CSF is thought to be contained in a complex with proteins, including apolipoprotein E. The present example demonstrates that antibodies to apoE, while able to bind to the complex, do not sequester apoE from the remainder of the complex.

ApoE complexes (500 ng) were incubated with Mab or polyclonal antibodies to apoE (2 μg) at 37° C. for one hour. The incubated samples were then subjected to NDGGE using the techniques described in Example 1. Following NDGGE, Western blotting was performed with affinity purified goat anti-apoE antibodies with detection by ECL. When no antibody is present, apoE can be detected at 8–13 nm consistent with its presence in lipoprotein particles. The presence of monoclonal or polyclonal antibodies to apoE results in a population shift of apoE to a larger molecular species, a "super shift". This demonstrates that the antibodies to apoE did not sequester, i.e., remove apoE from a lipoprotein particle, rather they bind to apoE on the lipoproteins creating a larger molecular species.

EXAMPLE 5

Sequestration of Aβ is Not Perturbed by Anti-apoE Antibodies

A sample of 100 μl human CSF was incubated either with Mab 266 alone, or with polyclonal anti-apoE, or with both antibodies for 60 minutes at 37° C. The samples were then analyzed by NDGGE as described in Example 1 and the detection of bands performed as described in Example 1.

The results show that as long as Mab 266 was added to the sample, the band at approximately 11 nm diameter characteristic of the sequestered 266-Aβ peptide complex was visible. This is the case whether or not anti-apoE is present. This band, demonstrating sequestered Aβ, also appears if 50 ng of Aβ peptide is added to the incubation mixture in the presence of Mab 266. Thus, alteration of the molecular weight of apoE by the presence of anti-apoE antibodies does not interfere with sequestration of Aβ peptide by Mab 266.

EXAMPLE 6

Sequestration of Aβ Peptide In Vivo

A. Transgenic $APP^{V717F}$ mice, also termed PDAPP mice, over-express a mutant form of human APP protein. These mice produce human Aβ in the CNS and have elevated levels of human Aβ peptide circulating in the CSF and plasma. Eight month old mice were injected intravenously with saline or 100 μg of Mab 266. They were bled 10 minutes after initial injection and again at 20 hours after initial injection.

Samples containing 20 μl of plasma from each animal were analyzed by NDGGE and Western blot with antibody 3D6 as described in Example 1. The saline injected animals did not show the presence of the characteristic 11 nm sequestered Aβ peptide band either after 10 minutes or 20 hours. However, the two animals that were injected with Mab 266 did show the appearance of this band after 20 hours.

B. Two month old $APP^{V717F}$ mice were used in this study. At day zero, the mice received either no Mab 266, 1 mg Mab 266, or 100 μg of this antibody. Plasma samples were taken two days prior to administration of the antibodies and on days 1, 3, 5 and 7. The plasma samples were subjected to NDGGE followed by Western blotting and detection with 3D6 as described in Example 1. At all time points following administration of Mab 266, the 266/Aβ complex was detected unless the plasma sample had been treated with protein G, which binds to immunoglobulin, thus effectively removing the Mab 266. Consistent levels of complex over the time period tested were found except for a slight drop-off at day seven in animals injected with 100 μg of Mab 266; in general, the levels in animals administered 100 μg were consistently lower than those found in the mice administered 1 mg of this antibody.

C. Two two-month old $APP^{V717F}$ mice were administered 1 mg of Mab 266 intravenously and a 25 μl plasma sample was taken from each. The plasma sample was subjected to NDGGE followed by Western blot as described above except that binding with biotinylated 3D6 was followed by detection with streptavidin$^{125}$I (Amersham) and exposure to a phosphorimaging screen. The level of complex was estimated in comparison to a standard curve using known amounts of $Aβ_{40}$ complexed with saturating levels of Mab 266 and detected similarly. The amount of Aβ peptide bound to Mab 266 was estimated at approximately 100 ng/ml, representing an increase of approximately 1,000-fold over endogenous Aβ peptide in these mice which had been determined to be about 100 pg/ml. This is also similar to the level of Aβ peptide in $APP^{V717F}$ brain prior to Aβ deposition (50–100 ng/g); human AβP and human Aβ in $APP^{V717F}$ Tg mice are produced almost solely in the brain. Thus, it appears that the presence of Mab 266 in the plasma acts as an Aβ peptide sink facilitating net efflux of Aβ peptide from the CNS into the plasma. This increased net efflux likely results from both increasing Aβ efflux from CNS to plasma and also from preventing Aβ in plasma from re-entering the brain.

The correct size for the sequestered Aβ peptide was confirmed by running 20 μL of plasma samples obtained from $APP^{V717F}$ mice 24 hours after being injected with 1 mg Mab 266 on TRIS-tricine SDS-PAGE gels followed by Western blotting using anti-Aβ antibody 6E10 prior to, or after, protein G exposure using protein G-bound beads. A band that was depleted by protein G was detected at 4–8 kD, consistent with the presence of monomers and possibly dimers of Aβ peptide.

D. Two month old $APP^{V717F}$ mice were treated with either PBS (n=7) or 500 μg biotinylated Mab 266—i.e., m266B (n=9) intraperitoneally. Both prior to and 24 hours after the injection, plasma was analyzed for total Aβ peptide using a modification of the ELISA method of Johnson-Wood, K., et al., *Proc. Natl. Acad. Sci. USA* (1997). 94:1550–1555; and Bales, K. R., et al., *Nature Genet* (1997) 17:263–264. Total Aβ bound to m266B was measured by using 96-well Optiplates (Packard, Inc.) coated with m3D6. Diluted plasma samples and standards (varying concentrations of $Aβ_{40}$ and m266B) were incubated overnight in the coated plates and the amount of total Aβ/m266B complex was determined with the use of $^{125}$I-Streptavidin. In addition, at the 24-hour time point, the plasma samples were first treated with protein G to quantitate Aβ peptide not bound to Mab 266, and $Aβ_{Total}$ and $Aβ_{42}$ were determined by ELISA in the CSF. In PBS-injected animals, plasma Aβ peptide levels were 140 pg/ml both before and after injection. Plasma levels were similar in the Mab 266-injected mice prior to injection, but levels of Aβ peptide not bound to Mab 266 were undetectable at 24 hours post injection.

Levels in the CSF were also measured, CSF represents an extracellular compartment within the CNS and concentration of molecules in the CSF reflects to some extent the concentration of substances in the extracellular space of the brain. CSF was isolated from the cisterna magna compartment. Mice were anesthetized with pentobarbital and the musculature from the base of the skull to the first vertebrae was removed. CSF was collected by carefully puncturing the arachnoid membrane covering the cistern with a micro needle under a dissecting microscope and withdrawing the CSF into a polypropylene micropipette. At 24 hours post injection, an increase in total Aβ peptide in the CSF of Mab 266-injected mice was found, and an approximately two-fold increase in A$\beta_{42}$ as compared to PBS injected mice was obtained in the CSF. This was confirmed using denaturing gel electrophoresis followed by Western blotting with A$\beta_{42}$-specific antibody 21F12.

In an additional experiment, three month old APP$^{V717F}$ Tg mice were injected with either PBS or Mab 266 intravenously and both A$\beta_{40}$ and A$\beta_{42}$ levels were assessed in the CSF as follows:

For measurement of A$\beta_{40}$, the monoclonal antibody m2G3, specific for A$\beta_{40}$ was utilized. The ELISA described (Johnson-Wood, K., et al., *Proc. Natl. Acad. Sci. USA* (1997) 94:1550–1555) was modified into an RIA by replacing the Streptavidin-HRP reagent with $^{125}$I-Streptavidin. For plasma and CSF samples, the procedure was performed under non-denaturing conditions that lacked guanidine in the buffers. For assessment of carbonate soluble and insoluble Aβ in brain homogenate, samples were homogenized with 100 mM carbonate, 40 mM NaCl, pH 11.5 (4° C.), spun at 10,000×g for 15 min, and Aβ was assessed in the supernatant (soluble) and the pellet (insoluble) fractions as described (Johnson-Wood, K., et al., *Proc. Natl. Acad. Sci. USA* (1997) 94:1550–1555) and listed above. The measurement of Aβ/Mab 266 complex in plasma was performed by a modified RIA. Mice were injected with biotinylated Mab 266 (Mab 266B) and plasma was isolated at multiple time points. Total Aβ bound to Mab 266 was measured by using 96-well Optiplates (Packard, Inc.) coated with m3D6. Diluted plasma samples and standards (varying concentrations of A$\beta_{40}$ and Mab 266B) were incubated overnight in the coated plates and the amount of total Aβ/Mab 266B complex was determined with the use of $^{125}$I-Streptavidin.

Three hours following the intravenous injection of Mab 266, there was a two-fold increase in CSF A$\beta_{40}$ levels and a non-significant increase in A$\beta_{42}$. However, at both 24 and 72 hours there was a two to three-fold increase in both A$\beta_{40}$ and A$\beta_{42}$ in the CSF. Similar results were obtained using denaturing gel analysis followed by Aβ Western blotting of pooled CSF. The efflux of Aβ through brain interstitial fluid, which is reflected to some degree by CSF levels, likely accounts for the observed increase in CSF Aβ.

It is significant that the change in CSF Aβ peptide levels cannot be due to entry of Mab 266 into the CSF since the levels measured 24 hours after injection, which are less than 0.1% plasma levels of Mab 266, are insufficient to account for the changes. These results suggest Aβ peptide is withdrawn from the brain parenchyma into the CSF by the presence of the antibody in the bloodstream.

Forms of Aβ peptide which are soluble in PBS or carbonate buffer were measured in cerebral cortical homogenates in the same mice which had been injected with Mab 266 and in which the CSF was analyzed as described above. Similar increases in these soluble forms in the cortical homogenates were observed.

EXAMPLE 7

Mab 266 Acts as an Aβ Peptide Sink In Vitro

A dialysis chamber was constructed as an in vitro system to test the ability of Mab 266 to act as a sink for Aβ peptide. One mL of human CSF was placed in the top chamber of a polypropylene tube separated by a dialysis membrane with a specified cutoff in the range 10–100 kD from a bottom chamber containing 75 μL PBS with or without 1 μg of Mab 266.

It appeared that equilibrium was reached after 3 hours, as determined by subjecting material in the bottom chamber to acid urea gels followed by Western blotting for Aβ peptide with 6E10 at various time points Samples were denatured in formic acid to a final concentration of 80% (vol/vol) and reduced with β-mercaptoethanol (1%). Samples were electrophoresed (anode to cathode) in a 0.9 M acetic acid running buffer through a 4% to 35% polyacrylamide gradient gel containing 6 M urea, 5% (vol/vol) glacial acetic acid, and 2.5% TEMED. The acidic pH of the gel was neutralized prior to transfer to nitrocellulose. Subsequently, standard Western blotting techniques were used to identify Aβ. The bands detected corresponded to 4 kD.

The amount of Aβ removed from the top chamber was thus determined by ELISA analysis of both top and bottom chambers (n=4) after 3 hours. The results for various molecular weight cutoffs in the presence and absence of Mab 266 are shown in FIG. 1. As shown, while only minimal amounts of Aβ peptide crossed the membrane when PBS was placed in the bottom chamber, 50% of the Aβ peptide was sequestered in the bottom chamber when Mab 266 was present and the molecular weight cutoff was 25 kD; increasing amounts crossed as the molecular weight cutoff increased to 100 kD, when almost 100% of the Aβ peptide was drawn across the membrane.

It was also observed that the anti-N-terminal Aβ antibodies 3D6 and 10D5 were able to draw Aβ peptide across the membrane in this system, though not able to sequester Aβ peptide in the assays described in Example 1. These results show that antibodies to the Aβ peptide have sufficient affinity under these conditions to sequester the peptide in physiological solutions away from other binding proteins, but that Mabs such as 266 which are immunoreactive with an epitope in positions 13–28 are substantially more efficient and bind with higher affinity.

In similar assays, astrocyte-secreted apoE4 which was purified as described by DeMattos, R. B., et al., *J. Biol. Chem.* (1998) 273:4206–4212; Sun, Y., et al., *J. Neurosci.* (1998) 18:3261–3272, had a small by statistically significant effect in increasing the mass of Aβ peptide in the bottom chamber. No apparent affect was observed when polyclonal IgG or BSA was substituted for Mab 266.

EXAMPLE 8

Flux of Aβ Peptide into Plasma from the CNS

A. One μg of A$\beta_{40}$ was dissolved into 5 μL of rat CSF to keep it soluble and was then injected into the subarachnoid space of the cisterna magna of wild-type Swiss-Webster mice which had previously received IV injections of either PBS (n=3) or 200 μg of biotinylated Mab 266 (n=3). At different time-points following treatment, A$\beta_{Total}$ in the plasma of the mice was determined by Aβ ELISA, using 3D6 as the coating antibody and standards of Aβ mixed with an excess of biotinylated 266. Each plasma sample was spiked with an excess of biotinylated 266 after removal from each animal for Aβ detection in the ELISA. In the PBS-injected mice, minimally detectable amounts of the peptide at levels of 0.15 ng/ml were detected as peak values after 30–60 minutes, after which the levels were essentially zero. In the mice administered Mab 266, however, plasma Aβ peptide reached levels 330-fold higher than those detected in PBS-injected mice after 60 minutes (approximately 50 ng/ml) and reached values of approximately 90 ng/ml after 180 minutes.

Figure 2:
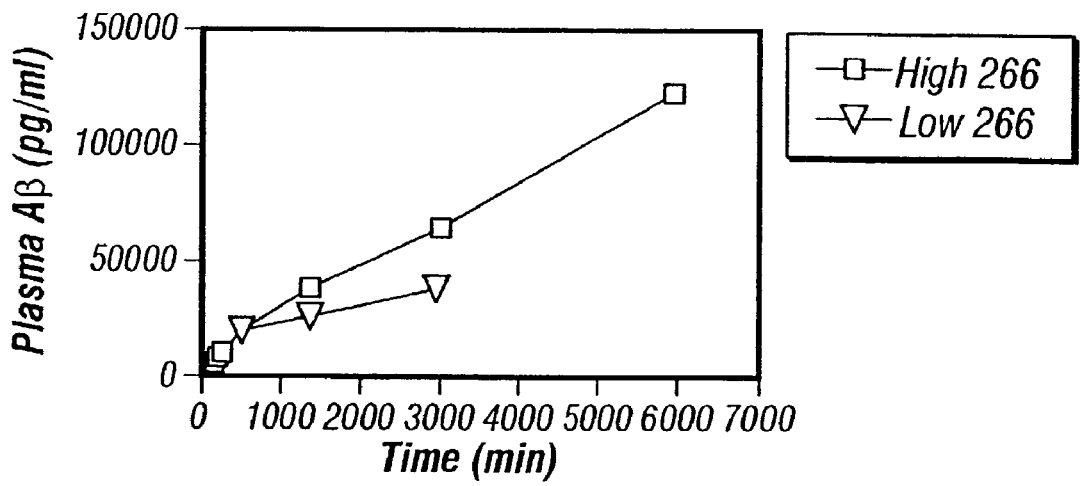
FIG. 2 shows the concentration of $Aβ_{Total}$ found in the plasma of an $APP^{V717F}$ transgenic mouse after injection with either 200 μg or 600 μg of Mab 266 as a function of time.

B. This procedure was repeated using either 200 μg (n=3) or 600 μg (n=3) injected IV into two-month-old APP$^{V717F}$ mice. Mab 266 was injected i.v. into 3 month old APP$^{V717F}$+/+mice with the above doses. Prior to and at different time-points following i.v. injection, the plasma concentration of Aβ bound to Mab 266 was determined by RIA. The detailed results from one illustrative mouse are shown in FIG. 2.

It was found that the concentration of Aβ bound to the monoclonal antibody Mab 266 increased from basal levels of 150 pg/ml to levels of over 100 ng/ml by four days. By analyzing early time points on the curve, it was determined that the net rate of entry of Aβ$_{Total}$ into plasma of the APP$^{V717F}$ Tg mice was 42 pg/ml/minute in the presence of saturating levels of the antibody.

The effects of Mab 266 on plasma Aβ levels in both wild type and APP$^{V717F}$ Tg mice as well as the effects of the antibody on Aβ concentration in CSF show that the presence of circulating Mab 266 results in a change in the equilibrium of Aβ flux or transport between the CNS and plasma.

EXAMPLE 9

Mab 266 Effect on Aβ in the Brain

Figure 3A:
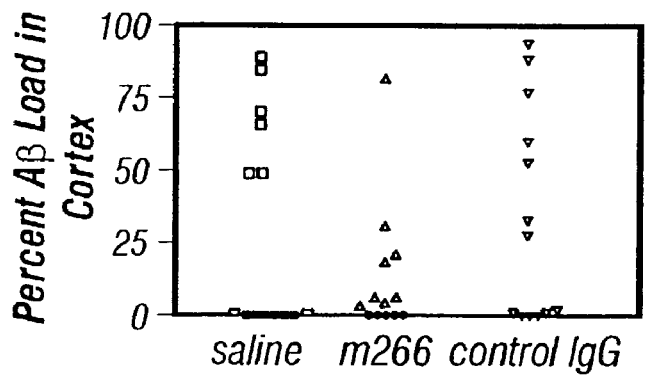
FIG. 3A shows the quantity of Aβ peptide deposition in the cortex in $APP^{V717F}$ transgenic mice treated with saline, mouse IgG, or Mab 266.
Figure 3B:
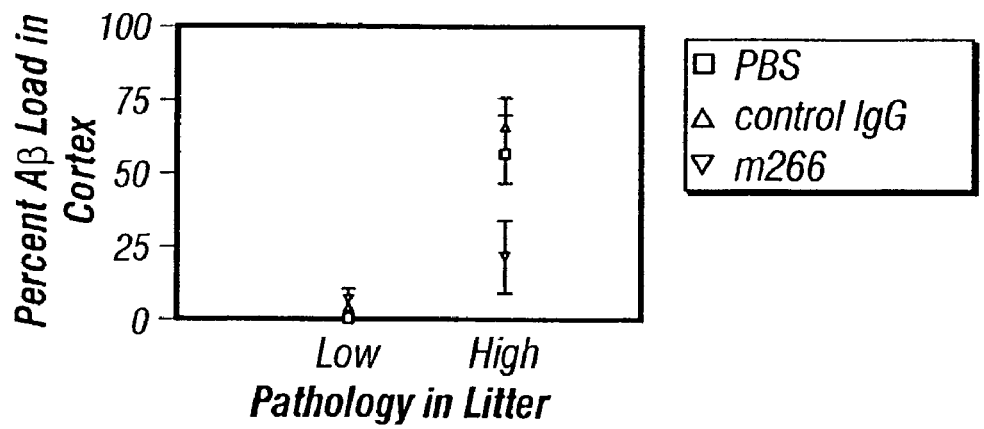
FIG. 3B shows correlation of these results with parental origin.

Four month old APP$^{V717F}$+/+ mice were treated every 2 weeks for 5 months with IP injections of saline, Mab 266 (500 μg), or control mouse IgG (100 μg, Pharmigen). The mice were sacrificed at nine months of age, and Aβ deposition in the cortex was determined. The % area covered by Aβ-immunoreactivity, as identified with a rabbit pan-Aβ antibody (QCB, Inc.), was quantified in the cortex immediately overlying the dorsal hippocampus as described by Holtzman, D. M., et al., *Ann. Neurol.* (2000) 97:2892–2897. The results are shown in FIG. 3A. At this age, about half of each group has still not begun to develop Aβ deposition. However, the % of mice with >50% Aβ burden in the cortex was significantly less (P=0.02, Chi-square test) in the 266-treated group. While APP$^{V717F}$ mice can develop large amounts of Aβ deposits by nine months, there is great variability with about 50% showing no deposits and about 50% showing substantial deposits. In PBS and IgG treated animals, 6/14 and 5/13 mice had greater than 50% of the cortex covered by Aβ staining, while only one of 14 mice treated with Mab 266 had this level of staining. Almost 50% of the animals in all groups still had not developed Aβ deposition by 9 months of age. The latter appears to be due to parental origin of individual mice in our cohort since even though all mice studied were confirmed to be APP$^{V717F+/+}$, high levels of Aβ deposition was observed only in mice derived from 4/8 breeding pairs (High pathology litters). Mice derived from the other 4 breeding pairs were virtually free of Aβ deposits (Low pathology litters). Using parental origin as a co-variate, there was a strong, significant effect of m266 in reducing Aβ deposition (p=0.0082, FIG. 3B).

EXAMPLE 10

Peripherally Injected Mab 266 Does Not Bind to Plagues in APP$^{V717F}$ Tg Mice

To determine whether Mab 266 injected i.p. over 5 months was bound to Aβ in brain, brain sections from 9 month old APP$^{V717F+/+}$ Tg mice which contained Aβ deposits and had been treated with either Mab 266, saline, or control IgG were utilized. Tissue processing and immunostaining was performed as described (Bales, K. R., et al., *Nature Genet.* (1997) 17:263–264). Tissue from all groups of animals was incubated with fluorescein-labeled anti-mouse IgG (Vector, Inc.) and then examined under a fluorescent microscope. No specific staining of Aβ deposits was seen in any of the groups. In contrast, when applying Mab 266 to sections prior to incubation of the sections with anti-mouse IgG, Aβ deposits were clearly detected.

EXAMPLE 11

Effect of Administration of Antibody 266 on Cognition in 24-Month Old Transgenic, Hemizygous PDAPP Mice Sixteen hemizygous transgenic mice (APP$^{V717F}$) were used. The mice were approximately 24 months old at the start of the study. All injections were intraperitoneal (i.p.). Half the mice received weekly injections of phosphate buffered saline (PBS, "Control") and the other half received 500 micrograms of mouse antibody 266 dissolved in PBS. Injections were made over a period of seven weeks (42 days) for a total of six injections. Three days following the last injection, the behavior of the animals was assessed using an object recognition task, essentially as described in J. -C. Dodart, et al., *Behavioral Neuroscience,* 113 (5) 982–990 (1999). A recognition index $(T_B \times 100)/(T_B - T_A)$ was calculated. Results are shown below in Table 1.

TABLE 1

Descriptive statistics for recognition index

| | | Recognition Index (minutes) | | |
|---|---|---|---|---|
| | N | Mean | Standard Deviation | Standard Error |
| Control (PBS) | 8 | 71.2** | 8.80 | 3.11 |
| Antibody 266 | 8 | 54.35 | 7.43 | 2.62 |

**p = 0.0010

Administration of 500 micrograms of antibody 266 weekly to 24 month old, hemizygous, transgenic mice was associated with a significant change in behavior. Antibody treated transgenic mice had recognition indices which were similar to wildtype control animals [J. -C. Dodart, et al]. The difference in the recognition index was statistically significant at the 0.001 probability level. The increased recognition index is an indication that treatment with an antibody that binds to the beta amyloid peptide in the region of amino acids 13–28 will reverse the behavioral impairments that had been documented in this mouse model of Alzheimer's Disease. Therefore, the administration of antibodies that bind beta amyloid peptide in the region of amino acids 13–28 will treat diseases such as Alzheimer's disease and Down's syndrome and will halt the cognitive decline typically associated with disease progression.

The amyloid burden (% area covered by immunoreactive material after staining with anti-Aβ antibodies 3D6 or 21F12) was quantified in the cortex immediately overlying the hippocampus including areas of the cingulate and parietal cortex from the brains of the 24 month-old animals treated with mouse antibody 266 for seven weeks, as described above. The results are presented in the table below. The differences between the treatment groups are not statistically significant.

TABLE 2

Amyloid plaque burden in APP$^{V717F+/-}$ mice following treatment with mouse 266 anti-Aβ antibody

| | | Plaque Burden (%) | | |
|---|---|---|---|---|
| | | Using 3D6 | | Using 21F12 |
| | N | Mean | Standard Error | Mean | Standard Error |
| Control (PBS) | 7 | 44.3 | 5.93 | 0.77 | 0.14 |
| Antibody 266 | 8 | 38.0 | 2.96 | 0.93 | 0.11 |

For these very old animals, treatment with mouse antibody 266 did not result in a significantly different amyloid burden compared with the PBS-treated group, measured using either 3D6 or using 21F12. Furthermore, the Aβ burden was substantially greater and significantly increased compared with the amyloid burden in younger animals (see below) who were not able to discriminate a novel object from a familiar one in the object recognition task. Most surprisingly, these results demonstrate that anti-Aβ antibodies can reverse cognitive deficits without the need to reduce amyloid burden per se.

After 7 weeks of treatment, the recognition index of the m266-treated group was not significantly different than what would be expected for a wild type cohort of 24 month old mice! This indicates a complete reversal of cognitive decline in these transgenic animals.

EXAMPLE 12

Effect of Administration of Antibody 266 on Cognition in Young Transgenic, Hemizygous PDAPP Mice Fifty-four (54) homozygous, transgenic mice (APP$^{V717F}$) were used. Twenty-three (23) mice were approximately two months old at the start of the study. The remaining mice were approximately four months old at the start of the study. The duration of treatment was five months. Thus, at study termination, the mice were either approximately seven (7) months old or approximately nine (9) months old.

All injections were intraperitoneal (i.p.). Each mouse in "PBS" control groups received a weekly injection of phosphate buffered saline (PBS; 200 μL). Each mouse in the "IgG" control groups received a weekly injection of IgG1κ1 isotype control (100 μg/mouse/week). Each mouse in the "High Dose" groups received a weekly injection of 500 microgram of antibody 266 dissolved in PBS ("HD"). Each mouse in the "Low Dose" group received a weekly injection of 100 micrograms of antibody 266 dissolved in PBS ("LD"). Three days following the last injection, the behavior of the animals was assessed using an object recognition task, as described in Example 10 above, and a discrimination index was calculated as the difference between the time spent on a novel object and the time spent on a familiar object. Results are shown below in Table 3. The data are grouped by the age of the mice at the end of the study.

TABLE 3

Descriptive statistics for discrimination index

| | | Discrimination Index (minutes) | | |
|---|---|---|---|---|
| | N | Mean | Standard Deviation | Standard Error |
| 7 months old | | | | |
| PBS | 7 | 2.12 | 4.22 | 1.59 |
| IgG | 8 | 0.81 | 3.64 | 1.29 |
| HD | 8 | 10.04* | 6.52 | 2.30 |
| 9 months old | | | | |
| PBS | 7 | 1.87 | 3.54 | 1.34 |
| IgG | 8 | 0.96 | 3.51 | 1.24 |
| LD | 8 | 10.75* | 6.44 | 2.28 |
| HD | 8 | 12.06*** | 7.82 | 2.76 |

*$p < 0.05$
***$p < 0.0001$

Taken together these data support the conclusion that administration of antibody 266, an antibody directed against the central domain of AP, attenuates plaque deposition in 7–9 month old APP$^{V717F}$ transgenic mice, as well as reverses the behavioral impairments previously characterized. Treatment of patients with an antibody directed against the central domain of the Aβ peptide will inhibit or prevent cognitive decline typically associated with disease progression, and will reverse it.

The discrimination index for treated animals was not significantly different than what would be expected for wild type mice of the same age. Thus, just as in older animals (Example 11), treatment with m266 completely reversed cognitive decline in these younger transgenic animals.

EXAMPLE 13

Synthesis of Humanized Antibody 266

Cells and antibodies. Mouse myeloma cell line Sp2/0 was obtained from ATCC (Manassas, Va.) and maintained in DME medium containing 10% FBS (Cat # SH32661.03, HyClone, Logan, Utah) in a 37° C. $CO_2$ incubator. Mouse 266 hybridoma cells were first grown in RPMI-1640 medium containing 10% FBS (HyClone), 10 mM HEPES, 2 mM glutamine, 0.1 mM non-essential amino acids, 1 mM sodium pyruvate, 25 μg/ml gentamicin, and then expanded in serum-free media (Hybridoma SFM, Cat # 12045–076, Life Technologies, Rockville, Md.) containing 2% low Ig FBS (Cat # 30151.03, HyClone) to a 2.5 liter volume in roller bottles. Mouse monoclonal antibody 266 (Mu266) was purified from the culture supernatant by affinity chromatography using a protein-G Sepharose column. Biotinylated Mu266 was prepared using EZ-Link Sulfo-NHS-LC-LC-Biotin (Cat # 21338ZZ, Pierce, Rockford, Ill.).

Cloning of variable region cDNAs. Total RNA was extracted from approximately $10^7$ hybridoma cells using TRIzol reagent (Life Technologies) and poly(A)$^+$ RNA was isolated with the PolyATract mRNA Isolation System (Promega, Madison, Wis.) according to the suppliers' protocols. Double-stranded cDNA was synthesized using the SMART™ RACE cDNA Amplification Kit (Clontech, Palo Alto, Calif.) following the supplier's protocol. The variable region cDNAs for the light and heavy chains were amplified by polymerase chain reaction (PCR) using 3' primers that anneal respectively to the mouse kappa and gamma chain constant regions, and a 5' universal primer provided in the SMARTTMRACE cDNA Amplification Kit. For VL PCR, the 3' primer has the sequence:

5'-TATAGAGCTCAAGCTTGGATGGTGGGAA-GATGGATACAGTTGGTGC-3' [SEQ ID NO:13] with residues 17–46 hybridizing to the mouse Ck region. For VH PCR, the 3' primers have the degenerate sequences:

```
                                       A   G  T
5'-TATAGAGCTCAAGCTTCCACTGGATAGACCGATGGGGCTGTCGTTTTGGC-3'    [SEQ ID NO:14]
                                       T
``` with residues 17–50 hybridizing to mouse gamma chain CH1. The VL and VH cDNAs were subcloned into pCR4Blunt-TOPO vector (Invitrogen, Carlsbad, Calif.) for sequence determination. DNA sequencing was carried out by PCR cycle sequencing reactions with fluorescent dideoxy chain terminators (Applied Biosystems, Foster City, Calif.) according to the manufacturer's instruction. The sequencing reactions were analyzed on a Model 377 DNA Sequencer (Applied Biosystems).

Construction of humanized 266 (Hu266) variable regions. Humanization of the mouse antibody V regions was carried out as outlined by Queen et al. [*Proc. Natl. Acad. Sci. USA* 86:10029–10033 (1988)]. The human V region framework used as an acceptor for Mu266 CDRs was chosen based on sequence homology. The computer programs ABMOD and ENCAD [Levitt, M., J. Mol. Biol. 168:595–620 (1983)] were used to construct a molecular model of the variable regions. Amino acids in the humanized V regions that were predicted to have contact with CDRs were substituted with the corresponding residues of Mu266. This was done at residues 46, 47, 49, and 98 in the heavy chain and at residue 51 in the light chain. The amino acids in the humanized V region that were found to be rare in the same V-region subgroup were changed to the consensus amino acids to eliminate potential immunogenicity. This was done at residues 42 and 44 in the light chain.

Figure 6:
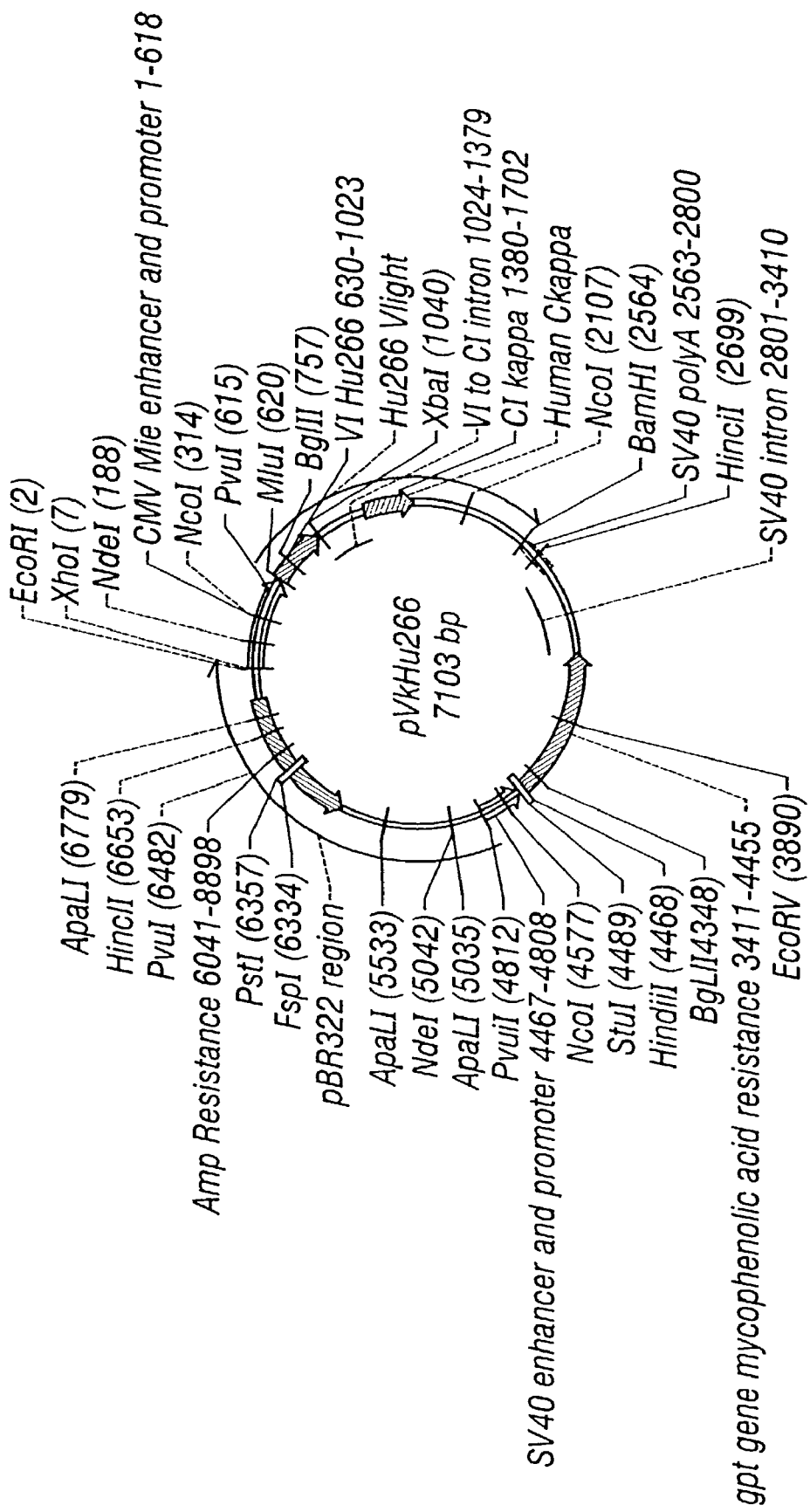
FIG. 6 is a plasmid map of pVk-Hu266.
Figure 7:
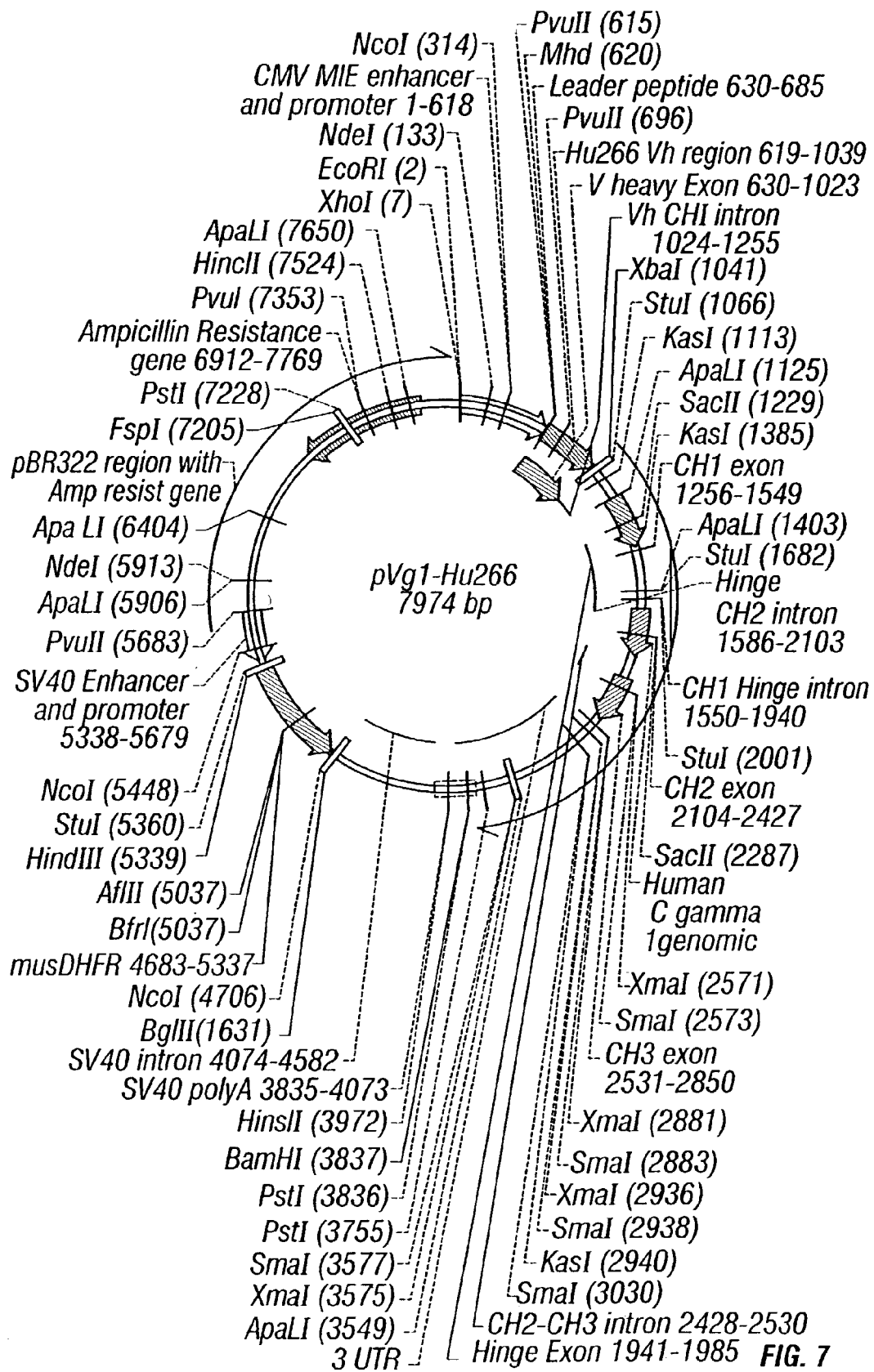
FIG. 7 is a plasmid map of pVg1-Hu266.

The light and heavy chain variable region genes were constructed and amplified using eight overlapping synthetic oligonucleotides ranging in length from approximately 65 to 80 bases [He, X. Y., et al., J. Immunol. 160: 029–1035 (1998)]. The oligonucleotides were annealed pairwise and extended with the Klenow fragment of DNA polymerase I, yielding four double-stranded fragments. The resulting fragments were denatured, annealed pairwise, and extended with Klenow, yielding two fragments. These fragments were denatured, annealed pairwise, and extended once again, yielding a full-length gene. The resulting product was amplified by PCR using the Expand High Fidelity PCR System (Roche Molecular Biochemicals, Indianapolis, Ind.). The PCR-amplified fragments were gel-purified and cloned into pCR4Blunt-TOPO vector. After sequence confirmation, the VL and VH genes were digested with MluI and XbaI, gel-purified, and subcloned respectively into vectors for expression of light and heavy chains to make pVk-Hu266 and pVg1-Hu266 (see FIGS. 6 and 7, respectively, herein) [Co, M. S., et al., J. Immunol. 148:1149–1154 (1992)]. The mature humanized 266 antibody expressed from these plasmids has the light chain of SEQ ID NO:11 and the heavy chain of SEQ ID NO:12.

Stable transfection. Stable transfection into mouse myeloma cell line Sp2/0 was accomplished by electroporation using a Gene Pulser apparatus (BioRad, Hercules, Calif.) at 360 V and 25 µF as described (Co et al., 1992). Before transfection, pVk-Hu266 and pVg1-Hu266 plasmid DNAs were linearized using FspI. Approximately $10^7$ Sp2/0 cells were transfected with 20 g of pVk-Hu266 and 40 µg of pVg1-Hu266. The transfected cells were suspended in DME medium containing 10% FBS and plated into several 96-well plates. After 48 hr, selection media (DME medium containing 10% FBS, HT media supplement, 0.3 mg/ml xanthine and 1 µg/ml mycophenolic acid) was applied. Approximately 10 days after the initiation of the selection, culture supernatants were assayed for antibody production by ELISA as shown below. High yielding clones were expanded in DME medium containing 10% FBS and further analyzed for antibody expression. Selected clones were then adapted to growth in Hybridoma SFM.

Measurement of antibody expression by ELISA. Wells of a 96-well ELISA plate (Nunc-Immuno plate, Cat # 439454, NalgeNunc, Naperville, Ill.) were coated with 100 µl of 1 µg/ml goat anti-human IgG, Fcγ fragment specific, polyclonal antibodies (Cat # 109-005-098, Jackson ImmunoResearch, West Grove, Pa.) in 0.2 M sodium carbonate-bicarbonate buffer (pH 9.4) overnight at 4° C. After washing with Washing Buffer (PBS containing 0.1% Tween 20), wells were blocked with 400 µl of Superblock Blocking Buffer (Cat # 37535, Pierce) for 30 min and then washed with Washing Buffer. Samples containing Hu266 were appropriately diluted in ELISA Buffer (PBS containing 1% BSA and 0.1% Tween 20) and applied to ELISA plates (100 µl per well). As a standard, humanized anti-CD33 IgG1 monoclonal antibody HuM195 (Co, et al., 1992, above) was used. The ELISA plate was incubated for 2 hr at room temperature and the wells were washed with Wash Buffer. Then, 100 µl of $\frac{1}{1,000}$-diluted HRP-conjugated goat antihuman kappa polyclonal antibodies (Cat # 1050-05, Southern Biotechnology, Birmingham, Ala.) in ELISA Buffer was applied to each well. After incubating for 1 hr at room temperature and washing with Wash Buffer, 100 µl of ABTS substrate (Cat #s 507602 and 506502, Kirkegaard and Perry Laboratories, Gaithersburg, Md.) was added to each well. Color development was stopped by adding 100 µl of 2% oxalic acid per well. Absorbance was read at 415 nm using an OPTImax microplate reader (Molecular Devices, Menlo Park, Calif.).

Purification of Hu266. One of the high Hu266-expressing Sp2/0 stable transfectants (clone 1D9) was adapted to growth in Hybridoma SFM and expanded to 2 liter in roller bottles. Spent culture supernatant was harvested when cell viability reached 10% or below and loaded onto a protein-A Sepharose column. The column was washed with PBS before the antibody was eluted with 0.1 M glycine-HCl (pH 2.5), 0.1 M NaCl. The eluted protein was dialyzed against 3 changes of 2 liter PBS and filtered through a 0.2 µm filter prior to storage at 4° C. Antibody concentration was determined by measuring absorbance at 280 nm (1 mg/ml=1.4 $A_{280}$). SDS-PAGE in Tris-glycine buffer was performed according to standard procedures on a 4–20% gradient gel (Cat # EC6025, Novex, San Diego, Calif.). Purified humanized 266 antibody is reduced and run on an SDSPAGE gel. The whole antibody shows two bands of approximate molecular weights 25 kDa and 50 kDa. These results are consistent with the molecular weights of the light chain and heavy chain or heavy chain fragment calculated from their amino acid compositions.

EXAMPLE 14

In Vitro Binding Properties of Humanized 266 Antibody

The binding efficacy of humanized 266 antibody, synthesized and purified as described above, was compared with the mouse 266 antibody using biotinylated mouse 266 antibody in a comparative ELISA. Wells of a 96-well ELISA plate (Nunc-immuno plate, Cat # 439454, NalgeNunc) were coated with 100 µl of β-amyloid peptide (1–42) conjugated to BSA in 0.2 M sodium carbonate/bicarbonate buffer (pH 9.4) (10 µg/mL) overnight at 4° C. The $A\beta_{1-42}$-BSA conjugate was prepared by dissolving 7.5 mg of $A\beta_{1-42}$-$Cys_{43}$ (C-terminal cysteine $A\beta_{1-42}$, AnaSpec) in 500 µL of dimethylsulfoxide, and then immediately adding 1,500 µL of distilled water. Two (2) milligrams of maleimide-activated bovine serum albumin (Pierce) was dissolved in 200 µL of distilled water. The two solutions were combined, thoroughly mixed, and allowed to stand at room temperature for two (2) hours. A gel chromatography column was used to separate unreacted peptide from $A\beta_{1-42}$-Cys-BSA conjugate.

After washing the wells with phosphate buffered saline (PBS) containing 0.1% Tween 20 (Washing Buffer) using an ELISA plate washer, the wells were blocked by adding 300 µL of SuperBlock reagent (Pierce) per well. After 30 minutes of blocking, the wells were washed Washing Buffer and excess liquid was removed.

A mixture of biotinylated Mu266 (0.3 µg/ml final concentration) and competitor antibody (Mu266 or Hu266; starting at 750 µg/ml final concentration and serial 3-fold dilutions) in ELISA Buffer were added in triplicate in a final volume of 100 µl per well. As a no-competitor control, 100 µl of 0.3 µg/ml biotinylated Mu266 was added. As a background control, 100 µl of ELISA Buffer was added. The ELISA plate was incubated at room temperature for 90 min. After washing the wells with Washing Buffer, 100 µl of 1 µg/ml HRP-conjugated streptavidin (Cat # 21124, Pierce) was added to each well. The plate was incubated at room temperature for 30 min and washed with Washing Buffer. For color development, 100 µl/well of ABTS Peroxidase Substrate (Kirkegaard & Perry Laboratories) was added. Color development was stopped by adding 100 µl/well of 2% oxalic acid. Absorbance was read at 415 nm. The absorbances were plotted against the log of the competitor concentration, curves were fit to the data points (using Prism) and the IC50 was determined for each antibody using methods well-known in the art.

The mean IC50 for mouse 266 was 4.7 µg/mL (three separate experiments, standard deviation=1.3 µg/mL) and for humanized 266 was 7.5 µg/mL (three separate experiments, standard deviation=1.1 µg/mL). A second set of three experiments were carried out, essentially as described above, and the mean IC50 for mouse 266 was determined to be 3.87 µg/mL (SD=0.12 µg/mL) and for human 266, the IC50 was determined to be 4.0 µg/mL (SD=0.5 µg/mL). On the basis of these results, we conclude that humanized 266 has binding properties that are very similar to those of the mouse antibody 266. Therefore, we expect that humanized 266 has very similar in vitro and in vivo activities compared with mouse 266 and will exhibit in humans the same effects demonstrated with mouse 266 in mice.

EXAMPLE 15

In Vitro Binding Properties of Mouse Antibodies 266 and 4G8

Antibody affinity (KD=Kd/Ka) was determined using a BIAcore biosensor 2000 and data analyzed with BIAevaluation (v. 3.1) software. A capture antibody (rabbit anti-mouse) was coupled via free amine groups to carboxyl groups on flow cell 2 of a biosensor chip (CM5) using N-ethyl-N-dimethylaminopropyl carbodiimide and N-hydroxysuccinimide (EDC/NHS). A non-specific rabbit IgG was coupled to flow cell 1 as a background control Monoclonal antibodies were captured to yield 300 resonance units (RU). Amyloid-beta 1–40 or 1–42 (Biosource International, Inc.) was then flowed over the chip at decreasing concentrations (1000 to 0.1 times KD). To regenerate the chip, bound anti-Aβ antibody was eluted from the chip using a wash with glycine-HCl (pH 2). A control injection containing no amyloid-beta served as a control for baseline subtraction. Sensorgrams demonstrating association and dissociation phases were analyzed to determine Kd and Ka. Using this method, the affinity of mouse antibody 266 for both $A\beta_{1-40}$ and for $A\beta_{1-42}$ was found to be 4 pM. The affinity of 4G8 for $A\beta_{1-40}$ was 23 nM and for $A\beta_{1-42}$ was 24 nM. Despite a 6000-fold difference in affinities for Aβ, both 266 and 4G8, which bind to epitopes between amino acids 13 and 28 of Aβ, effectively sequester Aβ from human CSF. Therefore, the location of the epitope is paramount, rather than binding affinity, in determining the ability of an antibody to sequester Aβ and to provide the beneficial and surprising advantages of the present invention.

EXAMPLE 16

Epitope Mapping of Mouse Antibody 266 Using Biacore Methodolgy and Soluble Peptides The BIAcore is an automated biosensor system for measuring molecular interactions [Karlsson R., et al. J. Immunol. Methods 145:229–240 (1991)]. The advantage of the BIAcore over other binding assays is that binding of the antigen can be measured without having to label or immobilize the antigen (i.e. the antigen maintains a more native conformation). The BIAcore methodology was used to assess the binding of various amyloid-beta peptide fragments to mouse antibody 266, essentially as described above in Example 12, except that all dilutions were made with HEPES buffered saline containing Tween 20, a variety of fragments of A□ (BioSource International) were injected, and a single concentration of each fragment was injected (440 nM).

Amyloid beta fragments 1–28, 12–28, 17–28 and 16–25 bound to mouse antibody 266, while Aβ fragments 1–20, 10–20, and 22–35 did not bind. Fragments 1–20, 10–20 and 22–35 bound to other MAbs with known epitope specificity for those regions of Aβ. Using this methodology, the binding epitope for the mouse antibody 266 appears to be between amino acids 17 and 25 of Aβ. Since binding usually occurs with at least 3 residues of the epitope present, one could further infer that the epitope is contained within residues 19–23.

EXAMPLE 17

In Vitro Binding Properties of Humanized Antibody 266

The affinity (KD=Kd/Ka) of humanized 266 antibody, synthesized and purified as described above, was determined essentially as described above in Example 15. Using this method, the affinity of humanized 266 for $A\beta_{1-42}$ was found to be 4 pM.

We claim:
1. A humanized antibody comprising:
(a) a light chain comprising a light chain variable region comprising the following sequence:

```
                                          (SEQ ID NO:7)
 1               5                  10
Asp Xaa Val Met Thr Gln Xaa Pro Leu Ser Leu Pro Val
        15                  20                  25
Xaa Xaa Gly Gln Pro Ala Ser Ile Ser Cys Arg Ser Ser
                30                  35
Gln Ser Leu Xaa Tyr Ser Asp Gly Asn Ala Tyr Leu His
 40                  45                  50
Trp Phe Leu Gln Lys Pro Gly Gln Ser Pro Xaa Leu Leu
        55                  60                  65
Ile Tyr Lys Val Ser Asn Arg Phe Ser Gly Val Pro Asp
                70                  75
Arg Phe Ser Gly Ser Gly Ser Gly Thr Asp Phe Thr Leu
 80                  85                  90
Lys Ile Ser Arg Val Glu Ala Glu Asp Xaa Gly Val Tyr
                95                  100
Tyr Cys Ser Gln Ser Thr His Val Pro Trp Thr Phe Gly
105                 110
Xaa Gly Thr Xaa Xaa Glu Ile Lys Arg
``` wherein:
Xaa at position 2 is Vle or Ile;
Xaa at position 7 is Ser or Thr;
Xaa at position 14 is Thr or Ser;
Xaa at position 15 is Leu or Pro;
Xaa at position 30 is Ile or Val;
Xaa at position 50 is Arg, Gln, or Lys;
Xaa at position 88 is Val or Leu;
Xaa at position 105 is Gln or Gly;
Xaa at position 108 is Lys or Arg; and
Xaa at position 109 is Val or Leu; and
(b) a heavy chain comprising a heavy chain variable region comprising the following sequence:

```
                                          (SEQ ID NO:8)
 1               5                  10
Xaa Val Gln Leu Val Glu Xaa Gly Gly Gly Leu Val Gln
        15                  20                  25
Pro Gly Gly Ser Leu Arg Leu Ser Cys Ala Ala Ser Gly
                30                  35
Phe Thr Phe Ser Arg Tyr Ser Met Ser Trp Val Arg Gln
 40                  45                  50
Ala Pro Gly Lys Gly Leu Xaa Leu Val Ala Gln Ile Asn
        55                  60                  65
Ser Val Gly Asn Ser Thr Tyr Tyr Pro Asp Xaa Val Lys
                70                  75
Gly Arg Phe Thr Ile Ser Arg Asp Asn Xaa Xaa Asn Thr
 80                  85                  90
Leu Tyr Leu Gln Met Asn Ser Leu Arg Ala Xaa Asp Thr
                95                  100
Ala Val Tyr Tyr Cys Ala Ser Gly Asp Tyr Trp Gly Gln
105                 100
Gly Thr Xaa Val Thr Val Ser Ser
``` wherein:
Xaa at position 1 is Glu or Gln;
Xaa at position 7 is Ser or Leu;
Xaa at position 46 is Glu, Val, Asp, or Ser;
Xaa at position 63 is Thr or Ser;
Xaa at position 75 is Ala, Ser, Val or Thr;
Xaa at position 76 is Lys or Arg;
Xaa at position 89 is Glu or Asp; and
Xaa at position 107 is Leu or Thr
and wherein the humanized antibody binds to an abeta peptide.

2. The humanized antibody of claim 1 comprising a light chain variable region of the sequence given by SEQ ID NO:9 and a heavy chain variable region given by SEQ ID NO:10.

3. The humanized antibody of claim 1 comprising a light chain of the sequence given by SEQ ID NO:11 and a heavy chain of the sequence given by SEQ ID NO:12.

4. The humanized antibody of claim 1 that is an IgG1 immunoglobulin isotype.

5. The humanized antibody of claim 1, wherein the antibody is produced in a host cell selected from the group consisting of a meyeloma cell, a chinese hamster ovary cell, a syrian hamster ovary cell, and a human embryonic kidney cell.

6. A pharmaceutical composition that comprises the humanized antibody of claim 1, and a pharmaceutically acceptable excipient.

7. A pharmaceutical composition that comprises the humanized antibody of claim 3, and a pharmaceutically acceptable excipient.

8. The humanized antibody of claim 1, wherein Xaa at position 30 of the light chain variable region is lie and wherein Xaa at position 63 of the heavy chain variable region is Thr.

9. The humanized antibody of claim 2 that is an IgG1 immunoglobulin isotype.

10. The humanized antibody of claim 3 that is an IgG1 immunoglobulin isotype.

11. The humanized antibody of claim 2, wherein the antibody is produced in a chinese hamster ovary cell.

12. The humanized antibody of claim 3, wherein the antibody is produced in a chinese hamster ovary cell.

* * * * *

UNITED STATES PATENT AND TRADEMARK OFFICE
CERTIFICATE OF CORRECTION

| | |
|---|---|
| PATENT NO. | : 7,195,761 B2 |
| APPLICATION NO. | : 10/226435 |
| DATED | : March 27, 2007 |
| INVENTOR(S) | : David M. Holtzman |

It is certified that error appears in the above-identified patent and that said Letters Patent is hereby corrected as shown below:

On the title page: item (60) should say: --Provisional application No. 60/184,601, filed on Feb. 24, 2000, provisional application No. 60/254,465, filed on Dec. 8, 2000, provisional application No. 60/254,498, filed on Dec. 8, 2000.--

Column 1, Line 11: correct the application no, "60/256,465" to --60/254,465-- such that Line 11 reads: --60/184,601, filed Feb. 24, 2000, 60/254,465 filed Dec. 8,--

Column 1, Line 22: correct the spelling of "angiopathy" to --angiopathy--: such that Line 22 reads: --Down's syndrome, and cerebral amyloid angiopathy. More--

Column 33, Line 26: insert the word --with-- after the word "washed" such that Line 26 reads: --of blocking, the wells were washed with Washing Buffer and--

Column 34, Line 43: correct the symbol "□" with a "β", such that Line 43 reads: --fragments of Aβ (BioSource International) were injected,--

Column 48, Claim 8, line 46: correct "lie" to "Ile" such that claim 8 reads: --8. The humanized antibody of claim 1, wherein Xaa at position 30 of the light chain variable region is Ile and wherein Xaa at position 63 of the heavy chain variable region is Thr.--

Signed and Sealed this

Eighth Day of May, 2007

JON W. DUDAS
*Director of the United States Patent and Trademark Office*

UNITED STATES PATENT AND TRADEMARK OFFICE
CERTIFICATE OF CORRECTION

PATENT NO. : 7,195,761 B2
APPLICATION NO. : 10/226435
DATED : March 27, 2007
INVENTOR(S) : David M. Holtzman et al.

It is certified that error appears in the above-identified patent and that said Letters Patent is hereby corrected as shown below:

Column 12, SEQ ID NO 9:

at position 42 please delete "Len" and insert --Leu--
at position 86 please delete "Gln" and insert --Glu--
at position 110 please delete "Gln" and insert --Glu--

Signed and Sealed this
First Day of January, 2013

David J. Kappos
*Director of the United States Patent and Trademark Office*

UNITED STATES PATENT AND TRADEMARK OFFICE
CERTIFICATE OF CORRECTION

PATENT NO. : 7,195,761 B2
APPLICATION NO. : 10/226435
DATED : March 27, 2007
INVENTOR(S) : David Holtzman and Ronald DeMattos Page 1 of 1

It is certified that error appears in the above-identified patent and that said Letters Patent is hereby corrected as shown below:

In the Specification

Insert Government Support Paragraph at Column 1, Line 15:
--STATEMENT REGARDING FEDERALLY SPONSORED RESEARCH OR DEVELOPMENT
This invention was made with government support under AG013956 awarded by the National Institutes of Health. The government has certain rights in the invention.--

Signed and Sealed this
Thirteenth Day of August, 2019

Andrei Iancu
*Director of the United States Patent and Trademark Office*